(12) United States Patent
Shames et al.

(10) Patent No.: US 7,858,592 B2
(45) Date of Patent: Dec. 28, 2010

(54) INTERFERING RNAS AGAINST THE PROMOTER REGION OF P53

(75) Inventors: David S. Shames, Dallas, TX (US); David R. Corey, Dallas, TX (US); Rachel S. Greer, Dallas, TX (US); John D. Minna, Dallas, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 94 days.

(21) Appl. No.: 12/035,982

(22) Filed: Feb. 22, 2008

(65) Prior Publication Data

US 2009/0099109 A1 Apr. 16, 2009

Related U.S. Application Data

(60) Provisional application No. 60/891,615, filed on Feb. 26, 2007.

(51) Int. Cl.
*A61K 48/00* (2006.01)
*A61K 35/00* (2006.01)
*C07H 21/02* (2006.01)
*C07H 21/04* (2006.01)

(52) U.S. Cl. .................. 514/44; 536/23.1; 536/24.5; 424/93.1

(58) Field of Classification Search .............. None
See application file for complete search history.

(56) References Cited

PUBLICATIONS

Brachman et al., Dominant-negative p53 mutations selected in yeast hit cancer hot spots, 1996, Proc. Natl. Acad. Sci., vol. 93, pp. 4091-4095.*
Bergamaschi et al., p53 polymorphism influences response in cancer chemotherapy via modulation of p73-dependent apoptosis, 2003, Cancer Cell, vol. 3, pp. 387-402.*
Bienz-Tadmor et al., "The 5' region of the p53 gene: evolutionary conservation and evidence for a negative regulatory element," *EMBO J.*, 4:3209-3213, 1985.
Bourdon et al., "p53 isoforms can regulate p53 transcriptional activity," *Genes Dev.*, 19:2122-2137, 2005.
Bumcrot et al., RNAi therapeutics: a potential new class of pharmaceutical drugs, *Nature Chemical Biology*, 2:711-719, 2006.
Garber, "Genetics. Small RNAs reveal an activating side," *Science*, 314:741-2, 2006.
Janowski et al., "Inhibiting gene expression at transcription start sites in chromosomal DNA with antigene RNAs," *Nature Chem. Biol.*, 1:216-222, 2005.
Janowski et al., "Inhibiting transcription of chromosomal DNA with antigene peptide nucleic acids," *Nature Chem. Biol.*, 1:210-215, 2005.
Janowski et al., "Involvement of AGO1 and AGO2 in mammalian transcriptional silencing," *Nat. Struct. Mol. Biol.*, 13:787-792, 2006.
Lamb and Crawford, "Characterization of the human p53 gene," *Molecular and Cellular Biology*, 6:1379-1385, 1986.
Li et al., "Small dsRNAs induce transcriptional activation in human cells," *PNAS*, 103:17337-17342, 2006.
Mills, "p53: link to the past, bridge to the future," *Genes and Development*, 19:2091-2099, 2005.
Rohaly et al., "A novel human p53 isoform is an essential element of the ATR-intra-S phase checkpoint," *Cell*, 122:21-32, 2005.
Song et al., "RNA interference targeting Fas protects mice from fulminant hepatitis," *Nat. Med.*, 9:347-351, 2003.
Soutschek et al., "Therapeutic silencing of an endogenous gene by systemic administration of modified siRNAs," *Nature*, 432, 173-8, 2004.
Tang, "siRNA and miRNA: an insight into RISCs," *Trends Biochem. Sci.*, 30:106-114, 2005.
Toub et al., "Innovative nanotechnologies for the delivery of oligonucleotides and siRNA," *Biomedicine and Pharmacotherapy*, 60:607-620, 2006.
Toyooka et al., "The TP53 gene, tobacco exposure, and lung cancer," *Hum. Mutat.*, 21:229-39, 2003.
Vogelstein et al., "Surfing the p53 network," *Nature*, 408:307-10, 2000.
Zimmerman et al., RNAi-mediated gene silencing in non-human primates, *Nature*, 441:111-4, 2006.

\* cited by examiner

*Primary Examiner*—Amy Bowman
(74) *Attorney, Agent, or Firm*—Fulbright & Jaworski

(57) ABSTRACT

The present invention relates to the inhibition of p53 transcription by interfering with the activity of a p53 promoter using inhibitory double-stranded RNAs. Use of these inhibitory RNAs in the treatment of cancers also is disclosed.

18 Claims, 13 Drawing Sheets

FIGS. 1A–B

Mutation Spectra for Cell Lines Used in this Study

5'-RACE and Blast Alignment for p53 Transcript in MCF7 and T47D

>Clone 1 MCF7
GCACGCTCCCAGCCCGAACGCAAAGTGTCCCCGGAGCCCAGCAGCTACCTGTCCCTGGACGGTGGCTCTAGAC
>Clone 2 MCF7
GCACGCTCCCAGCCCGAACGCAAAGTGTCCCCGGAGCCCAGCAGCTACCTGTCCCTGGACGGTGGCTCTAGAC
>Clone 1 T47D
GCACGCTCCCAGCCCGAACGCAAAGTGTCCCCGGAGCCCAGCAGCTACCTGTCCCTGGACGGTGGCTCTAGAC
>Clone 2 T47D
GCACGCTCCCAGCCCGAACGCAAAGTGTCCCCGGAGCCCAGCAGCTACCTGTCCCTGGACGGTGGCTCTAGAC

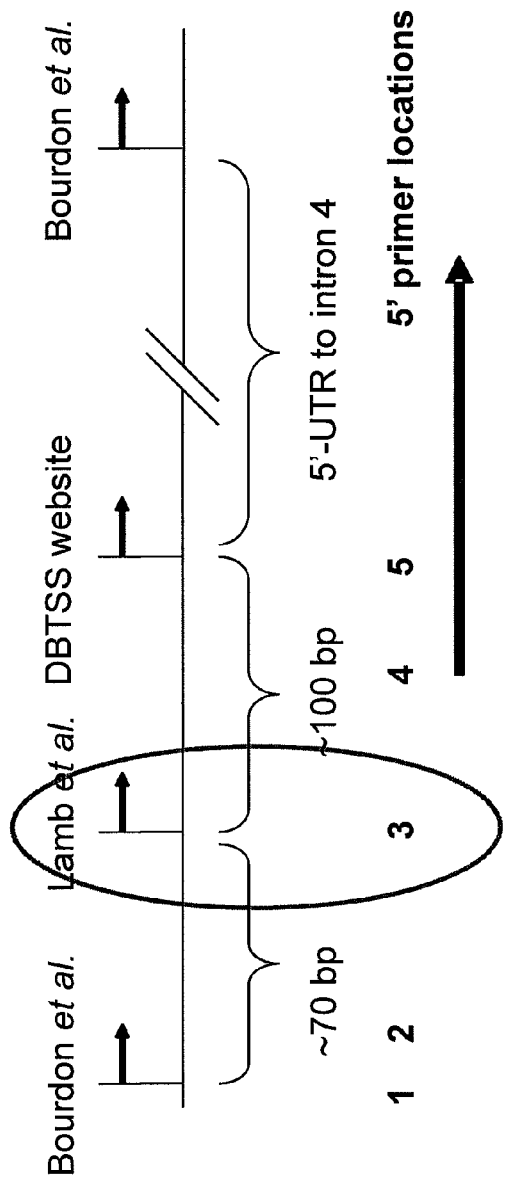

FIG. 3B

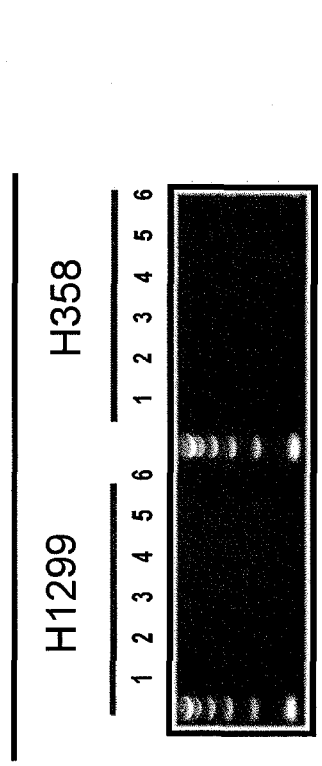
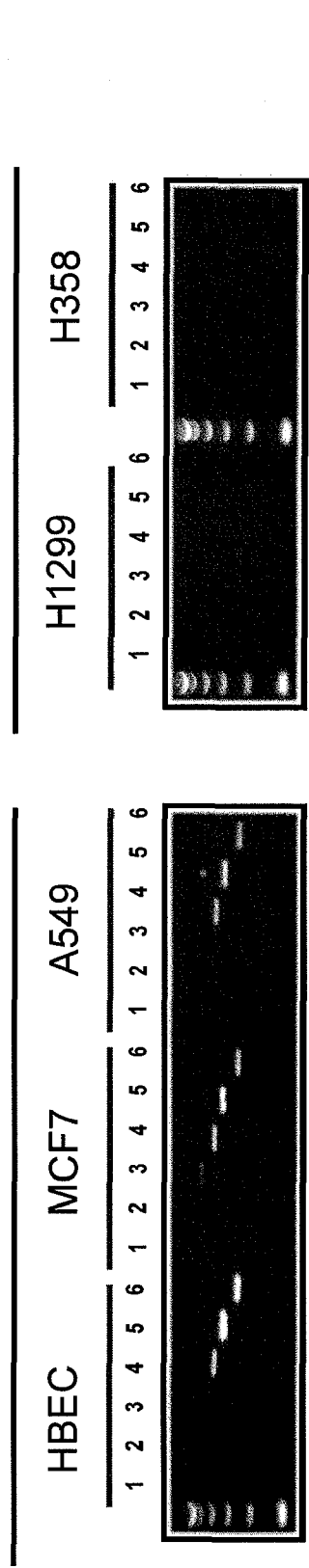
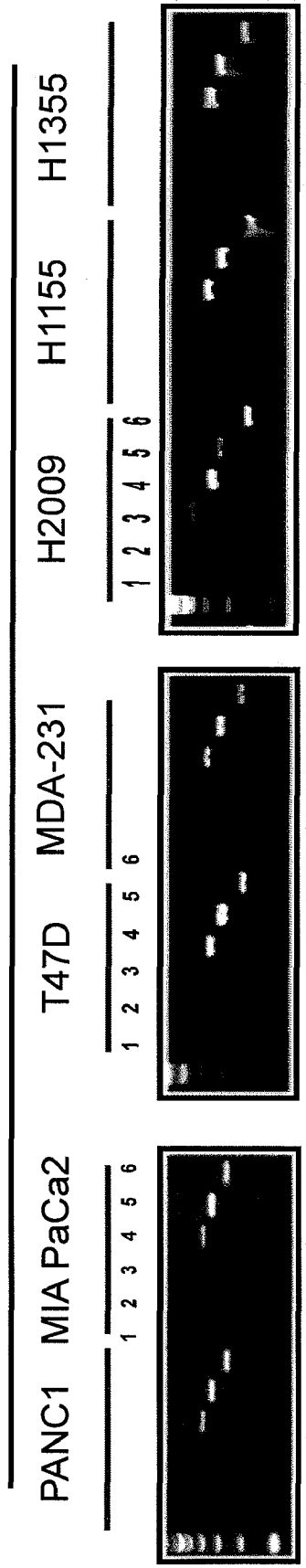
FIG. 3C

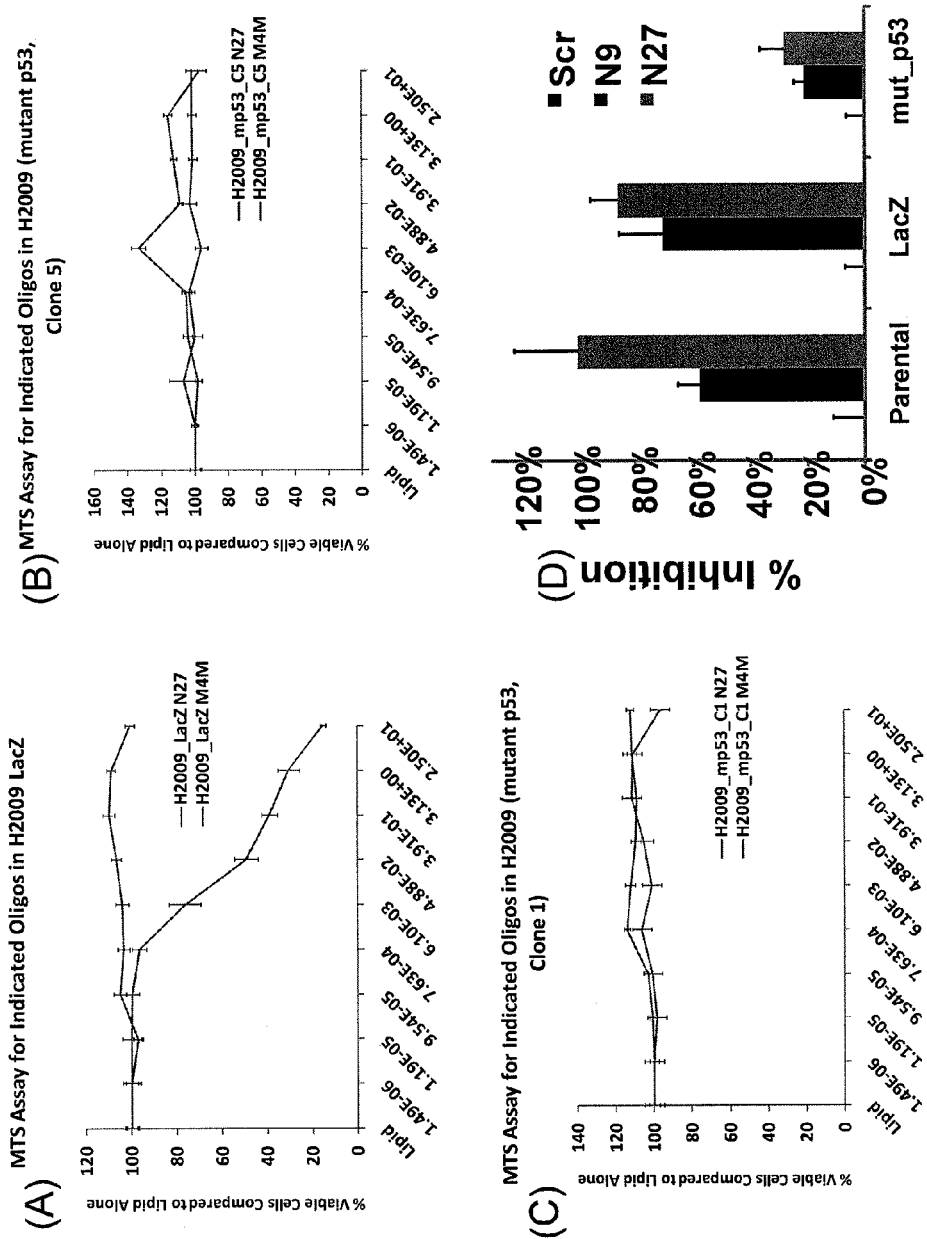
FIG. 7A-D

INTERFERING RNAS AGAINST THE PROMOTER REGION OF P53

PRIORITY CLAIM

This application claims benefit of priority U.S. Provisional Application Ser. No. 60/891,615, filed Feb. 26, 2007, the entire contents of which are hereby incorporated by reference.

STATEMENT REGARDING FEDERALLY SPONSORED RESEARCH OR DEVELOPMENT

This invention was made in part with government support under Grant No. P50CA75907 awarded by the National Cancer Institute. The United States Government has certain rights in the invention.

BACKGROUND OF THE INVENTION

A. Field of the Invention

The present invention relates to the fields of molecular biology, biochemistry, and oncology. More particularly, the invention provides for the inhibition of p53 transcription by interfering with the activity of a p53 promoter using inhibitory double-stranded RNAs.

B. Related Art p53 was identified some two decades ago as a tumor suppressor, and its mutation is implicated in at least 50% of all cancers. Though it has been the focus of intense research, new information continues to emerge about its complex biology. For example, it is now known that p53 is a member of a structurally-related family including p63 and p73, each of which expresses multiple RNA species with dozens of theoretic isoforms. p53 produces multiple mRNA alternative splice forms using at least four different promoters, one of which lies within intron #4, just upstream of exon 5. And though p53's normal role is in the inhibition of the cancer phenotype, the presence of dominant negative mutations in p53 can impede the normal apoptotic pathway that wild-type p53 induces, thereby resulting in resistance of certain cancers to other forms of therapy, such as radio- and chemotherapeutics.

Rohaly et al. (2005) reported on a novel p53 isoform present in most cells that is produced by alternative splicing of exons 7 through 9, designated as Δp53. This isoform transactivates the endogenous p21 and 14-3-3a promoters, but not the mdm2, bax or PIG3 promoters, and does so only in damaged S phase cells. Upon activation of the ATR-intra-S phase checkpoint, Δp53, but not p53, transactivates p21, resulting in downregulation of cyclin A-Cdk activity and attenuation of S phase progression. This results in uncoupling of repair and replication events. Interestingly, the region of Δp53 that is deleted is one where a large number of mutations occur, including those resulting in dominant negative mutants of p53. This region, identified as 257-323 of the wild-type sequence, lies at the C-terminal region of the DNA binding domain, and abuts the N-terminal region of the oligomerization domain. The ability of this isoform to function as a bona fide tumor suppressor gene remains to be determined.

SUMMARY OF THE INVENTION

Thus, in accordance with the present invention, there is provided a method of inhibiting a cancer cell comprising contacting said cancer cell with a duplex RNA that inhibits expression of a dominant-negative p53 expressed by said cancer cell. The cancer cell may be a breast cancer cell, a lung cancer cell, a prostate cancer cell, an ovarian cancer cell, a liver cancer cell, a uterine cancer cell, a stomach cancer cell, a colon cancer cell, a cervical cancer cell, a head & neck cancer cell, an esophageal cancer cell, a brain cancer cell, a pancreatic cancer cell, a testicular cancer cell, a skin cancer cell, a lymphoma cell, a leukemia cell, a sarcoma cell or a carcinoma cell. The duplex RNA may be 15-25 bases in length, and may comprise a sequence that is homologous to a transcriptional start site of said promoter. The sequence may hybridize to a region between nucleotides −50 to +25 from the gene's transcription start site, to a region between nucleotides −30 to +17 from the transcription start site, or to a region between nucleotides −15 to +10 from the transcription start site. In particular, the duplex RNA may comprise one of the sequences of SEQ ID NOS:1-20. The duplex RNA may be comprised within a lipid delivery vehicle; may have an $IC_{50}$ of $10^{-12}$; and/or may increase the expression of a Δp53 expressed by said cancer cell. Inhibiting may comprise inhibiting cell growth, cell replication, cell survival, metastasis, tissue invasion, or drug resistance, and in particular may comprise inducing cell death.

In another embodiment, there is provided a method of increasing the sensitivity of a cancer cell to an anti-cancer therapy comprising contacting said cancer cell with a duplex RNA that inhibits expression of a dominant-negative p53 expressed by said cancer cell. The cancer cell may be a breast cancer cell, a lung cancer cell, a prostate cancer cell, an ovarian cancer cell, a liver cancer cell, a uterine cancer cell, a colon cancer cell, a stomach cancer cell, a cervical cancer cell, a head & neck cancer cell, an esophageal cancer cell, a brain cancer cell, a pancreatic cancer cell, a testicular cancer cell, a skin cancer cell, a lymphoma cancer cell, a leukemia cell, a sarcoma cell or a carcinoma cell. The duplex RNA may be 15-25 bases in length; may comprise a sequence that is homologous to a transcriptional start site of said promoter. In particular, the duplex RNA may comprise one of the sequences of SEQ ID NOS:1-20. The duplex RNA may be comprised within a lipid delivery vehicle. The duplex RNA may increase the expression of a Δp53 expressed by said cancer cell. The anticancer therapy is a DNA damaging agent therapy. The method of claim 11, wherein said anticancer therapy may be a chemotherapy or radiotherapy. The method may further comprise contacting said cell with said anticancer therapy.

In still another embodiment, a method of treating a subject with cancer comprising administering to said subject a duplex RNA that inhibits expression of a dominant-negative p53 expressed by said cancer cell. The cancer may be breast cancer, lung cancer, prostate cancer, ovarian cancer, liver cancer, uterine cancer, cervical cancer, head & neck cancer, colon cancer, stomach cancer, esophageal cancer, brain cancer, pancreatic cancer, testicular cancer, skin cancer, lymphoma, leukemia, sarcoma or carcinoma. The duplex RNA may be 15-25 bases in length; may comprise a sequence that is homologous to a transcriptional start site of said promoter; and in particular may comprise one of the sequences of SEQ ID NOS: 1-20. The RNA may be comprised within a lipid delivery vehicle. Treatment may comprise reducing tumor size, reducing tumor growth, rendering a non-resectable tumor resectable, or inducing cell death in cells of said tumor. The method may further comprise administering to said subject a cancer therapy that induces DNA damage, such as chemotherapy or radiotherapy (e.g., x-irradiation, γ-irradiation, or microwave radiation). The duplex RNA may be administered more than once. The cancer may be multi-drug resistant, recurrent and/or metastatic.

In a further embodiment, there is provided a method of altering the expression of p53 isoforms in a cell comprising contacting said cell with a duplex RNA that targets a promoter that directs transcription of a p53 transcript. The promoter directs the transcription of a full length p53 transcript, such as a full length transcript encodes a mutant p53 polypeptide, and in particular a mutant p53 polypeptide that is a dominant-negative p53 polypeptide. The dominant-negative p53 polypeptide may be defective in DNA binding.

In still yet a further embodiment, there is provided a pharmaceutical composition comprising a duplex RNA that targets a promoter that directs transcription of a full length p53 transcript dispersed in a pharmaceutically acceptable buffer, diluent or excipient. The duplex RNA may be 15-25 bases in length, and/or may comprise a sequence that is homologous to a transcriptional start site of said promoter. The duplex RNA may comprise one of the sequences of SEQ ID NOS:1-20. The duplex RNA may be comprised within a lipid delivery vehicle. The sequence may hybridize to a region between nucleotides −100 to +25, between nucleotides −50 to +25, between nucleotides −30 to +17, or between nucleotides −15 to +10 from the transcription start site.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the following description and the accompanying drawings. It should be understood, however, that the following description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

BRIEF DESCRIPTION OF THE DRAWINGS

The following drawings form part of the present specification and are included to further demonstrate certain aspects of the present invention. The invention may be better understood by reference to these drawings and the detailed description presented below.

FIGS. 3A & 3C: Promoter structure for p53 gene locus. There are three functionally defined transcription start sites within 300 bp of the canonical p53 transcription start site as defined by Crawford and Lamb (1984). There is another downstream transcription start site found within intron 4 of the p53 gene locus, which was recently identified by Bourdon et al. (2005). This transcription start yields a N-terminal truncated p53 protein.

FIG. 3B: 5'-RACE and Blast Alignment for p53 Transcript in MCF7 and T47D (SEQ ID NO:21).

(FIG. 6A) HBECs and cell types other than lung cancer. (FIG. 6B) Lung cancer cell lines with differing p53 backgrounds. Oligonucleotides were titrated over the indicated concentrations (nM scale) using the reverse transfection method on day one and absorbance was measured on day 5 using the MTS reagent. Cell lines with wild-type p53 (A549) or null for p53 (H1299) are not affected by agRNA treatment, whereas the point-mutant p53 cell line (H1355) is sensitive p53 agRNA (SEQ ID NO:8). Estimated $IC_{50}$ for agRNA (SEQ ID NO:8) in H1355 is ~$3\times10^{-12}$ M. Blue diamond=M1; red square=scrambled oligo; green triangle=p53 siRNA; brown cross=p53 agRNA (SEQ ID NO:8); purple cross=p53 agRNA (SEQ ID NO:8).

FIGS. 7A-D: Genetic Rescue of Cells by Ectopic Mutant p53. (FIG. 7A) MTS assay for indicated oligos in H2009 LacZ. (FIG. 7B) MTS assay for indicated oligos in H2009 (mutant p53, clone 5). (FIG. 7C) MTS assay for indicated oligos in H2009 (mutant p53, clone 1). (FIG. 7D) Parent inhibition with indicated oligos in parental v. mutant p53 cell lines.

DETAILED DESCRIPTION OF THE INVENTION

Figure 1:
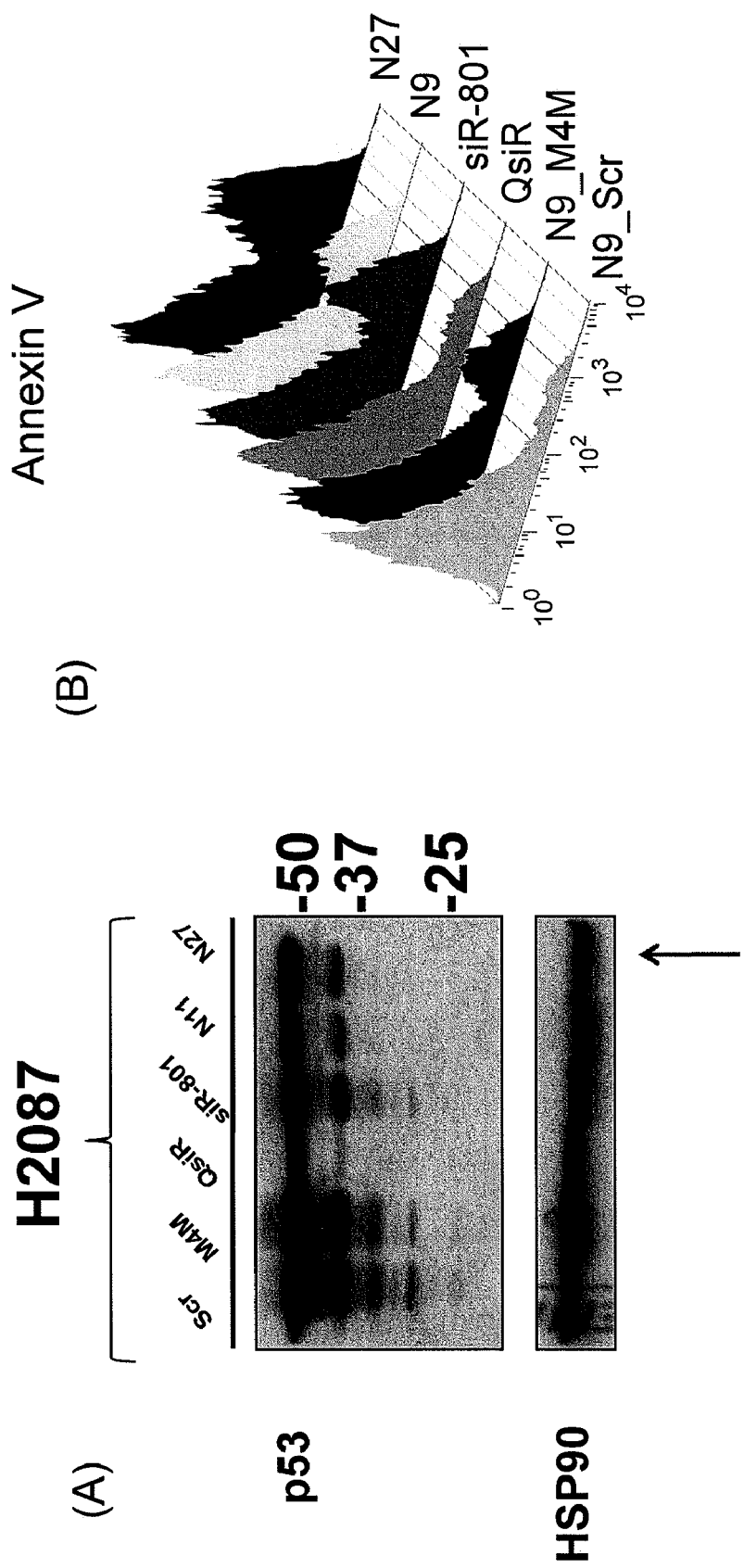
FIGS. 1A-B: agRNA to p53 Leads to Changes in p53 Isoform Levels and Induction of Apoptosis.

Previously, the inventors demonstrated that agRNAs are potent inhibitors of transcription in human cancer cells (Tang, 2004; Janowski et al., 2005a; Janowski et al., 2005b). Here, the inventors have focused on agRNAs that target the tumor suppressor p53. Unexpectedly, they have discovered that agRNAs directed against a p53 promoter gene not only reduced full-length p53 expression, but also increased expression of Δp53. This altered expression profile resulted in dramatic tumor cell kill, and also sensitized cells to treatment with other anticancer therapies including doxorubicin and other standard chemotherapies.

Several groups have treated cancers with full-length wild-type p53 gene therapy. However, the preclinical effects observed with agRNAs directed against the p53 promoter appear to be greater than that observed with traditional replacement gene therapy. Moreover, agRNAs do not require expression vectors for delivery, they work at low picomolar concentrations, and only affect tumors having p53 mutations, offering the possibility of great effect, as well as great specificity. Ongoing lung cancer clinical trials using systemic tumor suppressor gene therapy delivered in nanoparticles can easily be adapted to clinical testing of the disclosed agRNAs.

I. p53 and p53 Promoters

A. p53

When normal mammalian cells are subjected to stress signals (e.g., hypoxia, radiation, DNA damage or chemotherapeutic drugs), p53 is activated. In addition, ubiquitin-dependent degradation of the p53 protein is blocked. The resulting increase in p53-dependent gene transcription leads to p53-mediated induction of programmed cell death and/or cell cycle arrest. p53 is thought to provide a protective effect against tumorigenesis, and indeed, mutations of p53 have been found in nearly all tumor types and are estimated to contribute to around 50% of all cancers. Activation of p53 can result in cell cycle arrest, presumably to allow DNA repair to occur before replication or mitosis. In some cell types, however, p53 activation results in apoptosis as means of eliminating irreparably damaged cells. The final outcome of p53 activation depends on many factors, and is mediated largely through the action of downstream effector genes transactivated by p53.

There are four conserved domains in p53: (a) the N-terminal domain is required for transcriptional transactivation; (b) a sequence-specific DNA binding domain; (c) a tetramerization domain near the C-terminal end; (d) the C-terminal domain interacts directly with single stranded DNA. Wild-type p53 binds to specific genomic sites with a consensus binding site 5'-PuPuPuC(A/T)(T/A)GPyPyPy-3'. p53 binds as a tetramer and stimulates expression of downstream genes that negatively control growth and/or invasion or are mediators of apoptosis. It has been predicted that the expression of about 200-300 genes might ultimately be controlled by p53 transactivation.

p53 is activated in response to DNA damage, and many factors interact to signal and modulate this response. There is still controversy over the pathways that lead to the activation of p53. Several mechanisms have been suggested. One is that stress-activated protein kinases phosphorylate p53, protecting it from degradation and activating its function as a transcription factor. Indeed, many phosphorylated forms of p53 are found in cells, and by phosphorylation, p53 can be released from a latent state in which it cannot bind DNA. One attractive candidate for p53 activation by phosphorylation is the DNA-dependent protein kinase (DNA-PK). DNA-PK is activated by DNA damage, and one of its substrates is p53. DNA-PK phosphorylates Ser15 within the critical N-terminal region of p53, which controls the interaction of p53 with the transcriptional apparatus and with the MDM-2 protein. Indeed, recently it was demonstrated, that DNA-PK is required for the p53 response to occur (Woo et al., 1998). Also the ATM kinase, the product of the ATM gene (which is defective in patients with Ataxia Telangiectasia), phosphorylates Ser15 in vivo (Canman et al., 1998). Instead of its phosphorylation, the dephosphorylation of p53 at serine 376 by the ATM-dependent activation of a specific phosphatase might enable DNA binding of p53 and its transcriptional activation. In this process, the 14-3-3 proteins bind to the C-terminus of the dephosphorylated p53, possibly activating it.

Another pathway towards activation of p53 involves the mdm-2 gene product. MDM-2 can target p53 for nuclear export and degradation; nonfunctional MDM-2 results in accumulation of p53 and activation of p53-dependent transcription. The mdm-2 gene itself is activated for transcription by p53, so this model implies that p53 is constitutively active, driving transcription of the protein (MDM-2) that targets its own degradation. Blocking the p53 degradation pathway would result in the activation of the p53 response. Indeed, it was shown that the ARF tumor suppressor (also called p14$^{ARF}$) binds to the complex of p53 and MDM-2, by this stabilizing p53, possibly by inducing degradation of MDM-2 (Zhang et al., 1998). ARF expression itself is regulated by the E2F-1 transcription factor. This connects the Rb pathway to p53: oncogenes like E1A or SV40 T block Rb function, thus activating E2F-1. E2F-1 transcriptional activity leads to the expression of a number of genes required for passage into and through S phase but also to the expression of ARF which stabilizes p53. This would result in either p53 dependent apoptosis or cell cycle arrest unless p53 itself is inhibited, e.g., by the oncogenes E1B and SV40 T-antigen.

B. p53 Promoters

As discussed above, p53 is now known to use several different promoters and transcription start sites. Bourdon et al. (2005) reported that, in addition to the classical promoter and transcription start site defined by Crawford and Lamb, there are three more active promoters and transcription start sites. Two of these transcription start sites are near to the canonical p53 promoter and transcription start site and the third exists in intron 4 (Bourdon et al. 2005; Crawford and Lamb, 1984). Transcription from this downstream promoter results in a series of N-terminal truncated p53 isoforms collectively termed Δ133 isoforms. At present, it is unknown whether the upstream promoters and transcription start sites yield specific isoforms of p53. The different transcription start sites are predicted to result in different 5-UTRs. The structure of the p53 regulatory elements is shown in FIG. 6.

II. Inhibitory RNAs
  A. RNA Interference

RNA interference ($RNA_i$) is a form of gene silencing triggered by double-stranded RNA (dsRNA). RNAi has evolved myriad functions in eukaryotic cells including, defense from viral infections (plants and fungi), transposon activity (all eukaryotes), cellular differentiation, and organismal development. Fire et al. (1998); Grishok et al. (2000); Ketting et al. (1999); Lin & Avery (1999); Montgomery et al. (1998); Sharp (1999); Sharp & Zamore (2000); Tabara et al. (1999). RNAi is mediated by the Argonaute family of enzymes coupled with duplex RNAs that are complementary to target mRNAs. In mammalian cells, Argonaute 2 uses the duplex RNA to guide endonucleolytic cleavage of target mRNA. $RNA_i$ offers major experimental advantages for study of gene function. These advantages include a very high specificity, ease of movement across cell membranes, and prolonged down-regulation of the targeted gene. Fire et al. (1998); Grishok et al. (2000); Ketting et al. (1999); Lin & Avery (1999); Montgomery et al. (1998); Sharp (1999); Sharp & Zamore (2000); Tabara et al. (1999). Moreover, dsRNA has been shown to silence genes in a wide range of systems, including plants, protozoans, fungi, *C. elegans, Trypanasoma* and *Drosophila*. Grishok et al. (2000); Sharp (1999); Sharp & Zamore (1999).

The following description is incorporated herein because siRNAs, which induce RNAi, are similar in structure to agRNAs, and thus it is envisaged that some of the same synthetic methods and modifications will be used in their application as described below. WO 99/32619 and WO 01/68836 suggest that RNA for use in siRNA may be chemically or enzymatically synthesized. However, enzymatic synthesis is rarely used because of ease of obtaining commercially synthesized oligonucleotides. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Preferably, single-stranded RNA is enzymatically synthesized from the PCR products of a DNA template, preferably a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically- or enzymatically-synthesized siRNA.

siRNAs are now ordinarily obtained through commercial sources (Qiagen, Dharmacon, Ambion, ISIS). Chemical synthesis proceeds by making two single stranded RNA-oligomers followed by the annealing of the two single stranded oligomers into a double-stranded RNA. Non-limiting examples are provided in U.S. Pat. Nos. 5,889,136, 4,415,723, and 4,458,066, expressly incorporated herein by reference, and in Wincott et al. (1995).

Chemically synthesized siRNAs are found to work optimally when they are in cell culture at concentrations of 25-100 nM, but concentrations of about 100 pM have achieved effective suppression of expression in mammalian cells. (Caplen, et al., 2000; Elbashir et al., 2001).

U.S. Pat. No. 5,795,715 reports the simultaneous transcription of two complementary DNA sequence strands in a single reaction mixture, wherein the two transcripts are immediately hybridized. The templates used are preferably of between 40 and 100 base pairs, and which is equipped at each end with a promoter sequence. The templates are preferably attached to a solid surface. After transcription with RNA polymerase, the resulting dsRNA fragments may be used for detecting and/or assaying nucleic acid target sequences.

RNA-directed DNA methylation was described originally in plants (Matzke et al., 2004). The phenomenon was suggested by the finding that RNA viruses and viroids could induce methylation in genomic DNA sequences (Massenegger et al., 1994). RNA viruses and viroids produce only RNA during their lifecycles, clearly implicating RNA as the causative agent for methylation. Methylated bases were concentrated within sequences of DNA that were complementary to RNA, suggesting a sequence-specific mechanism for recognition (Pelissier and Wassenegger (2000).

In yeast, small RNAs that target centromere repeat sequences and mating type loci can silence gene expression by promoting modification of heterochromatin (Grewal and Moazed, 2003; Bernstein and Allis, 2005). Chromatin modifications involve methylation of histone H3 at Lysine 9 (Volpe et al., 2002) and require RNA-dependent RNA polymerase (Sugiyama et al., 2005) and DNA polymerase II (Schramke et al., 2005). Modification involves proteins of the RNA-induced transcriptional silencing (RITS) pathway (Verdel et al., 2003) including argonaute 1 (Sigova et al., 2004), a member of a protein family that is also involved in post-transcriptional silencing.

Recently, several other groups have suggested that so-called "anti-gene RNAs," or agRNAs, can also silence expression in mammalian cells. Kawasaki and Taira (2004) targeted ten duplex RNAs to sequences within the E-cadherin promoter that contained CpG dinucleotides. DNA methylation was observed at all of these sites. Individual RNAs yielded only marginal reductions in E-cadherin expression but more complete silencing could be achieved if all ten RNAs were combined. A link between methylation and silencing was supported by the observation that duplex RNAs were not able to inhibit expression of E-cadherin when methyl-transferase genes DMNT1 and DMNT3B were silenced. Importantly, these findings from this study were challenged and have not been reproduced independently. The original manscript has been retracted and the authors have been dismissed from their institution (Ting et al., 2005).

B. Peptide Nucleic Acids

Peptide nucleic acids (PNAs) are nonionic DNA mimics that have outstanding potential for recognizing duplex DNA (Kaihatsu et al., 2004; Nielsen et al., 1991). PNAs can be readily synthesized and bind to complementary sequences by standard Watson-Crick base-pairing (Egholm et al., 1993), allowing them to target any sequence within the genome without the need for complex synthetic protocols or design considerations. Strand invasion of duplex DNA by PNAs is not hindered by phosphate-phosphate repulsion and is both rapid and stable (Kaihatsu et al., 2004; Nielsen et al., 1991). Applications for strand invasion by PNAs include creation of artificial primosomes (Demidov et al., 2001), inhibition of transcription (Larsen and Nielsen, 1996), activation of transcription (Mollegaard et al., 1994), and directed mutagenesis (Faruqi et al., 1998). PNAs would provide a general and potent strategy for probing the structure and function of chromosomal DNA in living systems if their remarkable strand invasion abilities could be efficiently applied inside cells.

Strand invasion by PNAs in cell-free systems is most potent at sequences that are partially single-stranded (Bentin and Nielsen, 1996; Zhang et al., 2000). Assembly of RNA polymerase and transcription factors into the pre-initiation complex on DNA induces the formation of a structure known as the open complex that contains several bases of single-stranded DNA (Holstege et al., 1997; Kahl et al., 2000). The exceptional ability of PNAs to recognize duplex DNA allows them to intercept the open complex of an actively transcribed gene without a requirement for preincubation. The open complex is formed during transcription of all genes and PNAs can be synthesized to target any transcription initiation site. Therefore, antigene PNAs that target an open complex at a promoter region within chromosomal DNA would have the potential to be general tools for controlling transcription initiation inside cells.

III. Production of Inhibitory RNAs

A. Design

The present invention contemplates the production of inhibitory RNAs targeting p53 promoter regions. An exemplary RNA will comprise a 21-mer complementary to a sequence within about 200 bp of and 5' to a functional p53 transcription start site. Melting temperatures do not seem to be important for function. The design approach should avoid runs of more than 4 identical consecutive bases particularly near each end of the oligo. Terminal dTdT does not need to be complementary, nor is it absolutely necessary for functional activity. They are included for synthesis purposes as well as for price. Blast search sequence against the genome (not just coding) for homology to other sequences should be performed, and one should reject any sequences with >16 contiguous identical bases, or 10 contiguous bases in a 3'-UTR. Table 2 shows agRNAs that have been identified, produced and tested according to the present invention.

TABLE 1

Target sequences and melting temperatures of duplex RNAs

| | | |
|---|---|---|
| p53-N (-7) | AATGCACCCTCCTCCCCAACT | SEQ ID NO: 1 |
| p53-N (-9) | AATCTGCACCCTCCTCCCCAA | SEQ ID NO: 2 |
| p53-N (-11) | AAACTCTGCACCCTCCTCCCC | SEQ ID NO: 3 |
| p53-N (-15) | AACCTGACTCTGCACCCTCCT | SEQ ID NO: 4 |
| p53-N (-17) | AAATCCTGACTCTGCACCCTC | SEQ ID NO: 5 |
| p53-N (-19) | AAGAATCCTGACTCTGCACCC | SEQ ID NO: 6 |
| p53 N (21) | AAGAGAATCCTGACTCTGCAC | SEQ ID NO: 7 |
| p53-(-p53-N (-23) | AAGCGAGAATCCTGACTCTGC | SEQ ID NO: 8 |
| p53-N (-25) | AACGGCGAGAATCCTGACTCT | SEQ ID NO: 9 |
| p53-N (-27) | AAGTCGGCGAGAATCCTGACT | SEQ ID NO: 10 |
| p53-N (-29) | AAAGGTCGGCGAGAATCCTGA | SEQ ID NO: 11 |
| p53-N (-31) | AACCAGGTCGGCGAGAATCCT | SEQ ID NO: 12 |
| N9-Scr | AAAGCTTCTCAAAAAGTTTTG | SEQ ID NO: 13 |
| N27-Scr | AATGACTGTCGGCATCCAGAA | SEQ ID NO: 14 |
| N27-M4M | AAGACGGAGAGACTCGTGACT | SEQ ID NO: 15 |
| N9-M4M | AATGGACCCACCTGCCCATCT | SEQ ID NO: 16 |
| p53 siR-1 | AACCTACCAGGGCAGCTACGG | SEQ ID NO: 17 |
| p53 siR-2 | AAGGAAATTTGCGTGTGGAGT | SEQ ID NO: 18 |
| p53 siR-3 | AATCTACTGGGACGGAACAGC | SEQ ID NO: 19 |
| p53 siR-4 | AAAACAGCTTTGAGGTGCGTG | SEQ ID NO: 20 |

There are a variety of modifications that can be made to inhibitory RNAs to increase their efficacy, often by improving their stability. For example stability against nuclease degradation has been achieved by introducing a phosphorothioate (P=S) backbone linkage at the 3' end for exonuclease resistance and 2' modifications (2'-OMe, 2'-F and related) for endonuclease resistance (WO 2005115481; Li et al., 2005; Choung et al., 2006). A dsRNA motif having entirely of 2'-O-methyl and 2'-fluoro nucleotides has shown enhanced plasma stability and increased in vitro potency (Allerson et al., 2005). The incorporation of 2'-O-Me and 2'-O-MOE in dsRNA does not have a notable effect on activity (Prakash et al., 2005). Sugar modifications such as 2'-O-Me, 2'-F and locked nucleic acid (LNA, with a methylene bridge connecting 2' and 4' carbons) seem to be able to reduce the immunostimulatory effects of siRNAs (Bumcrot et al., 2006).

Duplexes containing a 4'-thioribose modification have been shown to have a stability 600 times greater than that of natural RNA (Hoshika et al, 2004). Crystal structure studies reveal that 4'-thioriboses adopt conformations very similar to the C3'-endo pucker observed for unmodified sugars in the native duplex (Haeberli et al., 2005). Stretches of 4'-thio-RNA were well tolerated in both the guide and nonguide strands. However, optimization of both the number and the placement of 4'-thioribonucleosides is necessary for maximal potency. These optimized siRNAs are generally equipotent with or superior to native siRNAs and show increased thermal and plasma stability. Furthermore, substantial improvements in siRNA activity and plasma stability have been achieved by judicious combination of 4'-thioribose with 2'-O-Me and 2'-O-MOE modifications (Dande et al., 2006). 2',5'-phosphodiester linkages seem to be tolerated in the nonguide but not the guide strand of the siRNA (Prakash et al., 2006).

In the boranophosphate linkage, a non-bridging phosphodiester oxygen is replaced by an isoelectronic borane (BH3-) moiety. Boranophosphate siRNAs have been synthesized by enzymatic routes using T7 RNA polymerase and a boranophosphate ribonucleoside triphosphate in the transcription reaction. Boranophosphate siRNAs are more active than native siRNAs if the center of the guide strand is not modified, and they may be at least ten times more nuclease resistant than unmodified siRNAs (Hall et al., 2004; Hall et al., 2006).

siRNA duplexes containing the 2,4-difluorotoluoyl ribonucleoside (rF) have been synthesized to evaluate the effect of noncanonical nucleoside mimetics on RNA interference. Thermal melting analysis showed that the base pair between rF and adenosine is destabilizing relative to a uridine-adenosine pair, although it is slightly less destabilizing than other mismatches. The crystal structure of a duplex containing rF-adenosine pairs shows local structural variations relative to a canonical RNA helix. As the fluorine atoms cannot act as hydrogen bond acceptors and are more hydrophobic than uridine, a well-ordered water structure is not seen around the rF residues in both grooves. Rapid amplification of 5 complementary DNA ends (5'-RACE) analysis confirms cleavage of target mRNA opposite to the rF placement site (Xia et al., 2006; Somoza et al., 2006).

Certain terminal conjugates have been reported to improve or direct cellular uptake. For example, siRNAs conjugated with cholesterol improve in vitro and in vivo cell permeation in liver cells (Rand et al., 2005). Soutschek et al. (2004) have reported on the use of chemically-stabilized and cholesterol-conjugated siRNAs have markedly improved pharmacological properties in vitro and in vivo. Chemically-stabilized siRNAs with partial phosphorothioate backbone and 2'-O-methyl sugar modifications on the sense and antisense strands (discussed above) showed significantly enhanced resistance towards degradation by exo- and endonucleases in serum and in tissue homogenates, and the conjugation of cholesterol to the 3' end of the sense strand of a siRNA molecule by means of a pyrrolidine linker (thereby generating chol-siRNA) did not result in a significant loss of gene-silencing activity in cell culture. Binding of chol-siRNAs to human serum albumin (HSA) was determined by surface plasmon resonance measurement, and while unconjugated siRNAs demonstrated no measurable binding to HSA, chol-siRNAs bound to HSA with an estimated dissociation constant of 1 mM. Presumably because of enhanced binding to serum proteins, chol-siRNAs administered to rats by i.v. injection showed improved in vivo pharmacokinetic properties as compared to unconjugated siRNAs. These study demonstrates that cholesterol conjugation significantly improves in vivo pharmacological properties of siRNAs.

B. Production dsRNA can be synthesized using well-described methods (Fire et al., 1998), but are generally obtained from commercial sources such as IDT, Ambion, Dharmacon, Qiagen, etc.

RNA oligonucleotides may be synthesized using commercially available 5'-O-(4,4'-dimethoxytrityl)-3'-O-(2-cyanoethyl-N,N-diisopropyl) phosphoramidite monomers of uridine (U), 4-N-benzoylcytidine ($C^{Bz}$), 6-N-benzoyladenosine ($A^{Bz}$) and 2-Nisobutyrylguanosine ($G^{iBu}$) with 2'-O-t-butyldimethylsilyl protected phosphoramidites and the corresponding 2'-O-methyl phosphoramidites according to standard solid phase oligonucleotide synthesis protocols. After cleavage and de-protection, RNA oligonucleotides can be purified by anion-exchange high-performance liquid chromatography, and characterized by ES mass spectrometry and capillary gel electrophoresis. RNA with phosphorothioate backbone at a given position can be achieved by oxidation of phosphite with Beaucage reagent during oligonucleotide synthesis (Soutschek et al., 2004).

CholsiRNAs may be synthesized using the same protocols as above except that the RNA synthesis started from a controlled-pore glass solid support carrying a cholesterol-aminocaproic acid-pyrrolidine linker. For this support, the first nucleotide linkage can be achieved using a phosphorothioate linkage to provide additional 3'-exonuclease stability. To generate siRNAs from RNA single strands, equimolar amounts of complementary sense and antisense strands are mixed and annealed, and siRNAs may be further characterized by native gel electrophoresis (Soutschek et al., 2004).

IV. Treatment of Cancers

The present invention also involves the treatment of cancer. The types of cancers that may be treated, according to the present invention, is limited only by the involvement of p53. Thus, it is contemplated that a wide variety of p53-mutated tumors may be treated using these therapies, including cancers of the brain, lung, liver, spleen, kidney, lymph node, pancreas, small intestine, blood cells, colon, stomach, breast, endometrium, prostate, testicle, ovary, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

A. Formulations and Routes for Administration to Patients

Where clinical applications are contemplated, it will be necessary to prepare pharmaceutical compositions in a form appropriate for the intended application. Generally, this will entail preparing compositions that are essentially free of pyrogens, as well as other impurities that could be harmful to humans or animals.

One will generally desire to employ appropriate salts, buffers, and lipids to render delivery of the oligonucleotides to allow for uptake by target cells. Such methods an compositions are well known in the art, for example, as disclosed in U.S. Pat. Nos. 6,747,014 and 6,753,423. Compositions of the present invention comprise an effective amount of the oligonucleotide to cells, dissolved or dispersed in a pharmaceutically acceptable carrier or medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents, liposomes, cationic lipid formulations, microbubble nanoparticles, and the like. The use of such media and agents for pharmaceutically active substances is well-known in the art. I'm not so sure this is true. Delivery is a major issue in the field. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by intradermal, subcutaneous, intramuscular, intraperitoneal or intravenous injection. Such compositions would normally be administered as pharmaceutically acceptable compositions, described supra. Of particular interest is direct intratumoral administration, perfusion of a tumor, or administration local or regional to a tumor, for example, in the local or regional vasculature or lymphatic system, or in a resected tumor bed (e.g., post-operative catheter). For practically any tumor, systemic delivery also is contemplated. This will prove especially important for attacking microscopic or metastatic cancer.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

The active compounds may also be administered as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, lipids, nanoparticles, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the oligonucleotides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

Of particular interest to the present invention is the use of lipid delivery vehicles. Lipid vehicles encompass micelles, microemulsions, macroemulsions, liposomes, and similar carriers. The term micelles refers to colloidal aggregates of amphipathic (surfactant) molecules that are formed at a well-defined concentration known as the critical micelle concentration. Micelles are oriented with the nonpolar portions at the interior and the polar portions at the exterior surface, exposed to water. The typical number of aggregated molecules in a micelle (aggregation number) is 50 to 100. Microemulsions are essentially swollen micelles, although not all micellar solutions can be swollen to form microemulsions. Microemulsions are thermodynamically stable, are formed spontaneously, and contain particles that are extremely small. Droplet diameters in microemulsions typically range from 10 100 nm. In contrast, the term macroemulsions refers to droplets with diameters greater than 100 nm. Liposomes are closed lipid vesicles comprising lipid bilayers that encircle aqueous interiors. Liposomes typically have diameters of 25 nm to 1 µm (see, e.g., Shah, 1998; Janoff, 1999).

In one embodiment of a liposome formulation, the principal lipid of the vehicle may be phosphatidylcholine. Other useful lipids include various natural (e.g., tissue derived L-α-phosphatidyl: egg yolk, heart, brain, liver, soybean) and/or synthetic (e.g., saturated and unsaturated 1,2-diacyl-SN-glycero-3-phosphocholines, 1-acyl-2-acyl-SN-glycero-3-phosphocholines, 1,2-diheptanoyl-SN-glycero-3-phosphocholine) derivatives of the same. Such lipids can be used alone, or in combination with a secondary lipid. Such secondary helper lipids may be non-ionic or uncharged at physiological pH, including non-ionic lipids such as cholesterol and DOPE (1,2-dioleolylglyceryl phosphatidylethanolamine). The molar ratio of a phospholipid to helper lipid can range from about 3:1 to about 1:1, from about 1.5:1 to about 1:1, and about 1:1.

Another specific lipid formulation comprises the SNALP formulation, containing the lipids 3-N-[(ω methoxypoly(ethylene glycol)$_{2000}$)carbamoyl]-1,2-dimyristyloxy-propylamine(PEG-C-DMA), 1,2-dilinoleyloxy-N,N-dimethyl-3-aminopropane (DLinDMA), 1,2-distearoyl-sn-glycero-3-phosphocholine (DSPC) and cholesterol, in a 2:40:10:48 molar % ratio. See Zimmerman et al. (2006).

A liposome is, in simplest form, composed of two lipid layers. The lipid layer may be a monolayer, or may be multilamellar and include multiple layers. Constituents of the liposome may include, for example, phosphatidylcholine, cholesterol, phosphatidylethanolamine, etc. Phosphatidic acid, which imparts an electric charge, may also be added. Exemplary amounts of these constituents used for the production of the liposome include, for instance, 0.3 to 1 mol, 0.4 to 0.6 mol of cholesterol; 0.01 to 0.2 mol, 0.02 to 0.1 mol of phosphatidylethanolamine; 0.0 to 0.4 mol, or 0-0.15 mol of phosphatidic acid per 1 mol of phosphatidylcholine.

Liposomes can be constructed by well-known techniques (see, e.g., Gregoriadis (1993). Lipids are typically dissolved in chloroform and spread in a thin film over the surface of a tube or flask by rotary evaporation. If liposomes comprised of a mixture of lipids are desired, the individual components are mixed in the original chloroform solution. After the organic solvent has been eliminated, a phase consisting of water optionally containing buffer and/or electrolyte is added and the vessel agitated to suspend the lipid. Optionally, the suspension is then subjected to ultrasound, either in an ultrasonic bath or with a probe sonicator, until the particles are reduced in size and the suspension is of the desired clarity. For transfection, the aqueous phase is typically distilled water and the suspension is sonicated until nearly clear, which requires several minutes depending upon conditions, kind, and quality of the sonicator. Commonly, lipid concentrations are 1 mg/ml of aqueous phase, but could be higher or lower by about a factor of ten.

Lipids, from which the solvents have been removed, can be emulsified by the use of a homogenizer, lyophilized, and melted to obtain multilamellar liposomes. Alternatively, unilamellar liposomes can be produced by the reverse phase evaporation method (Szoka and Papahadjopoulos, 1978). Unilamellar vesicles can also be prepared by sonication or extrusion. Sonication is generally performed with a bath-type sonifier, such as a Branson tip sonifier (G. Heinemann Ultrashall und Labortechnik, Schwabisch Gmund, Germany) at a controlled temperature as determined by the melting point of the lipid. Extrusion may be carried out by biomembrane extruders, such as the Lipex Biomembrane Extruder (Northern Lipids Inc, Vancouver, British Columbia, Canada). Defined pore size in the extrusion filters may generate unilamellar liposomal vesicles of specific sizes. The liposomes can also be formed by extrusion through an asymmetric ceramic filter, such as a Ceraflow Microfilter (commercially available from the Norton Company, Worcester, Mass.).

Following liposome preparation, the liposomes that have not been sized during formation may be sized by extrusion to achieve a desired size range and relatively narrow distribution of liposome sizes. A size range of about 0.2-0.4 microns will allow the liposome suspension to be sterilized by filtration through a conventional filter (e.g., a 0.22 micron filter). The filter sterilization method can be carried out on a high throughput basis.

Several techniques are available for sizing liposomes to a desired size, including, ultrasonication, high-speed homogenization, and pressure filtration (Hope et al., 1985; U.S. Pat. Nos. 4,529,561 and 4,737,323). Sonicating a liposome suspension either by bath or probe sonication produces a progressive size reduction down to small unilamellar vesicles less than about 0.05 microns in size. Multilamellar vesicles can be recirculated through a standard emulsion homogenizer until selected liposome sizes, typically between about 0.1 and 0.5 microns. The size of the liposomal vesicles may be determined by quasi-elastic light scattering (QELS) (see Bloomfield, 1981). Average liposome diameter may be reduced by sonication of formed liposomes. Intermittent sonication cycles may be alternated with QELS assessment to guide efficient liposome synthesis.

Liposomes can be extruded through a small-pore polycarbonate membrane or an asymmetric ceramic membrane to yield a well-defined size distribution. Typically, a suspension is cycled through the membrane one or more times until the desired liposome size distribution is achieved. The liposomes may be extruded through successively smaller-pore membranes, to achieve a gradual reduction in liposome size. For use in the present invention, liposomes have a size of about 0.05 microns to about 0.5 microns, or having a size of about 0.05 to about 0.2 microns.

B. Combined Therapy with Immunotherapy, Traditional Chemo- or Radiotherapy

One goal of current cancer research is to find ways to improve the efficacy of chemo- and radiotherapy, such as by combining traditional therapies with other anti-cancer treatments. For example, the herpes simplex-thymidine kinase (HS-tk) gene, when delivered to brain tumors by a retroviral vector system, successfully induced susceptibility to the antiviral agent gancyclovir (Culver et al., 1992). In the context of the present invention, it is contemplated that agRNA therapy could be used similarly in conjunction with chemotherapy, radiotherapeutic, immunotherapeutic, or other therapeutic intervention.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with an inhibitor according to the present invention and at least one other agent. These compositions would be provided in a combined amount effective to kill or inhibit proliferation of the cell. This process may involve contacting the cells with an agRNA according to the present invention and the other agent(s) or treatment(s) at the same time. This may be achieved by contacting the cell with a single composition or pharmacological formulation that includes both modalities, or by contacting the cell with two distinct compositions or formulations, at the same time, wherein one composition includes an agRNA according to the present invention and the other includes the secondary agent/therapy.

Alternatively, the agRNA therapy treatment may precede or follow the other agent/treatment by intervals ranging from minutes to weeks. In embodiments where the other agent and the agRNA are applied separately to the cell, one would generally ensure that a significant period of time did not expire between the time of each delivery, such that the agent/therapy and the agRNA would still be able to exert an advantageously combined effect on the cell. In such instances, it is contemplated that one would contact the cell with both modalities within about 12-24 hours of each other and, more preferably, within about 6-12 hours of each other, with a delay time of only about 12 hours being most preferred. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

It also is conceivable that more than one administration of either the inhibitor of p53 transcription or the other agent will be desired. Various combinations may be employed, where an agRNA according to the present invention is "A" and the other agent is "B," as exemplified below:

A/B/A  B/A/B  B/B/A  A/A/B  B/A/A  A/B/B  B/B/B/A

B/B/A/B  A/A/B/B  A/B/A/B  A/B/B/A  B/B/A/A  B/A/B/A

B/A/A/B  B/B/B/A  A/A/A/B  B/A/A/A  A/B/A/A  A/A/B/A

A/B/B/B  B/A/B/B  B/B/A/B

Other combinations are contemplated. Again, to achieve cell killing, both agents/therapies are delivered to a cell in a combined amount effective to kill the cell.

1. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

i. Alkylating Agents

Alkylating agents are drugs that directly interact with genomic DNA to prevent the cancer cell from proliferating. This category of chemotherapeutic drugs represents agents that affect all phases of the cell cycle, that is, they are not phase-specific. Alkylating agents can be implemented to treat chronic leukemia, non-Hodgkin's lymphoma, Hodgkin's disease, multiple myeloma, and particular cancers of the breast, lung, and ovary. They include: busulfan, chlorambucil, cisplatin, cyclophosphamide (cytoxan), dacarbazine, ifosfamide, mechlorethamine (mustargen), and melphalan. Troglitazaone can be used to treat cancer in combination with any one or more of these alkylating agents, some of which are discussed below.

a. Busulfan

Busulfan (also known as myleran) is a bifunctional alkylating agent. Busulfan is known chemically as 1,4-butanediol dimethanesulfonate.

Busulfan is not a structural analog of the nitrogen mustards. Busulfan is available in tablet form for oral administration. Each scored tablet contains 2 mg busulfan and the inactive ingredients magnesium stearate and sodium chloride.

Busulfan is indicated for the palliative treatment of chronic myelogenous (myeloid, myelocytic, granulocytic) leukemia. Although not curative, busulfan reduces the total granulocyte mass, relieves symptoms of the disease, and improves the clinical state of the patient. Approximately 90% of adults with previously untreated chronic myelogenous leukemia will obtain hematologic remission with regression or stabilization of organomegaly following the use of busulfan. It has been shown to be superior to splenic irradiation with respect to survival times and maintenance of hemoglobin levels, and to be equivalent to irradiation at controlling splenomegaly.

b. Chlorambucil

Chlorambucil (also known as leukeran) is a bifunctional alkylating agent of the nitrogen mustard type that has been found active against selected human neoplastic diseases. Chlorambucil is known chemically as 4-[bis(2-chlorethyl) amino] benzenebutanoic acid.

Chlorambucil is available in tablet form for oral administration. It is rapidly and completely absorbed from the gastrointestinal tract. After single oral doses of 0.6-1.2 mg/kg, peak plasma chlorambucil levels are reached within one hour and the terminal half-life of the parent drug is estimated at 1.5 hours. 0.1 to 0.2 mg/kg/day or 3 to 6 mg/m$^2$/day or alternatively 0.4 mg/kg may be used for antineoplastic treatment. Treatment regimes are well know to those of skill in the art and can be found in the "Physicians Desk Reference" and in "Remington's Pharmaceutical Sciences" referenced herein.

Chlorambucil is indicated in the treatment of chronic lymphatic (lymphocytic) leukemia, malignant lymphomas including lymphosarcoma, giant follicular lymphoma and Hodgkin's disease. It is not curative in any of these disorders but may produce clinically useful palliation. Thus, it can be used in combination with troglitazone in the treatment of cancer.

c. Cisplatin/Carboplatin

Cisplatin has been widely used to treat cancers such as metastatic testicular or ovarian carcinoma, advanced bladder cancer, head or neck cancer, cervical cancer, lung cancer or other tumors. Cisplatin can be used alone or in combination with other agents, with efficacious doses used in clinical applications of 15-20 mg/m$^2$ for 5 days every three weeks for a total of three courses. Exemplary doses may be 0.50 mg/m$^2$, 1.0 mg/m$^2$, 1.50 mg/m$^2$, 1.75 mg/m$^2$, 2.0 mg/m$^2$, 3.0 mg/m$^2$, 4.0 mg/m$^2$, 5.0 mg/m$^2$, 10 mg/m$^2$. Of course, all of these dosages are exemplary, and any dosage in-between these points is also expected to be of use in the invention.

Cisplatin is not absorbed orally and must therefore be delivered via injection intravenously, subcutaneously, intratumorally or intraperitoneally.

d. Cyclophosphamide

Cyclophosphamide is 2H-1,3,2-Oxazaphosphorin-2-amine, N,N-bis(2-chloroethyl)tetrahydro-, 2-oxide, monohydrate; termed Cytoxan available from Mead Johnson; and Neosar available from Adria. Cyclophosphamide is prepared by condensing 3-amino-1-propanol with N,N-bis(2-chlorethyl) phosphoramidic dichloride [(ClCH$_2$CH$_2$)$_2$N—POCl$_2$] in dioxane solution under the catalytic influence of triethylamine. The condensation is double, involving both the hydroxyl and the amino groups, thus effecting the cyclization.

Unlike other β-chloroethylamino alkylators, it does not cyclize readily to the active ethyleneimonium form until activated by hepatic enzymes. Thus, the substance is stable in the gastrointestinal tract, tolerated well and effective by the oral and parental routes and does not cause local vesication, necrosis, phlebitis or even pain.

Suitable doses for adults include, orally, 1 to 5 mg/kg/day (usually in combination), depending upon gastrointestinal tolerance; or 1 to 2 mg/kg/day; intravenously, initially 40 to 50 mg/kg in divided doses over a period of 2 to 5 days or 10 to 15 mg/kg every 7 to 10 days or 3 to 5 mg/kg twice a week or 1.5 to 3 mg/kg/day. A dose 250 mg/kg/day may be administered as an antineoplastic. Because of gastrointestinal adverse effects, the intravenous route is preferred for loading. During maintenance, a leukocyte count of 3000 to 4000/mm$^3$ usually is desired. The drug is also administered intramuscularly, by infiltration or into body cavities. It is available in dosage forms for injection of 100, 200 and 500 mg, and tablets of 25 and 50 mg the skilled artisan is referred to "Remington's Pharmaceutical Sciences" 15th Edition, chapter 61, incorporate herein as a reference, for details on doses for administration.

e. Melphalan

Melphalan, also known as alkeran, L-phenylalanine mustard, phenylalanine mustard, L-PAM, or L-sarcolysin, is a phenylalanine derivative of nitrogen mustard. Melphalan is a bifunctional alkylating agent which is active against selective human neoplastic diseases. It is known chemically as 4-[bis (2-chloroethyl)amino]-L-phenylalanine.

Melphalan is the active L-isomer of the compound and was first synthesized in 1953 by Bergel and Stock; the D-isomer, known as medphalan, is less active against certain animal tumors, and the dose needed to produce effects on chromosomes is larger than that required with the L-isomer. The racemic (DL-) form is known as merphalan or sarcolysin. Melphalan is insoluble in water and has a pKa$_1$ of ~2.1. Melphalan is available in tablet form for oral administration and has been used to treat multiple myeloma.

Available evidence suggests that about one third to one half of the patients with multiple myeloma show a favorable response to oral administration of the drug.

Melphalan has been used in the treatment of epithelial ovarian carcinoma. One commonly employed regimen for the treatment of ovarian carcinoma has been to administer melphalan at a dose of 0.2 mg/kg daily for five days as a single course. Courses are repeated every four to five weeks depending upon hematologic tolerance (Smith and Rutledge, 1975; Young et al., 1978). Alternatively the dose of melphalan used could be as low as 0.05 mg/kg/day or as high as 3 mg/kg/day or any dose in between these doses or above these doses. Some variation in dosage will necessarily occur depending on the condition of the subject being treated. The person responsible for administration will, in any event, determine the appropriate dose for the individual subject ii. Antimetabolites Antimetabolites disrupt DNA and RNA synthesis. Unlike alkylating agents, they specifically influence the cell cycle during S phase. They have been used to combat chronic leukemias in addition to tumors of breast, ovary and the gastrointestinal tract. Antimetabolites include 5-fluorouracil (5-FU), cytarabine (Ara-C), fludarabine, gemcitabine, and methotrexate. 5-Fluorouracil (5-FU) has the chemical name of 5-fluoro-2,4(1H,3H)-pyrimidinedione. Its mechanism of action involves blocking the methylation of deoxyuridylic acid to thymidylic acid. Thus, 5-FU interferes with the synthesis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

iii. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include bleomycin, dactinomycin, daunorubicin, doxorubicin (adriamycin), and idarubicin, some of which are discussed in more detail below. Widely used in clinical setting for the treatment of neoplasms these compounds are administered through bolus injections intravenously at doses ranging from 25-75 mg/m$^2$ at 21 day intervals for adriamycin, to 35-100 mg/m$^2$ for etoposide intravenously or orally.

a. Doxorubicin

Doxorubicin hydrochloride, 5,12-Naphthacenedione, (8s-cis)-10-[(3-amino-2,3,6-trideoxy-a-L-lyxo-hexopyranosyl)oxy]-7,8,9,10-tetrahydro-6,8,11-trihydroxy-8-(hydroxyacetyl)-1-methoxy-hydrochloride (hydroxydaunorubicin hydrochloride, adriamycin) is used in a wide antineoplastic spectrum. It binds to DNA and inhibits nucleic acid synthesis, inhibits mitosis and promotes chromosomal aberrations.

Administered alone, it is the drug of first choice for the treatment of thyroid adenoma and primary hepatocellular carcinoma. It is a component of 31 first-choice combinations for the treatment of ovarian, endometrial and breast tumors, bronchogenic oat-cell carcinoma, non-small cell lung carcinoma, gastric adenocarcinoma, retinoblastoma, neuroblastoma, mycosis fungoides, pancreatic carcinoma, prostatic carcinoma, bladder carcinoma, myeloma, diffuse histiocytic lymphoma, Wilms' tumor, Hodgkin's disease, adrenal tumors, osteogenic sarcoma soft tissue sarcoma, Ewing's sarcoma, rhabdomyosarcoma and acute lymphocytic leukemia. It is an alternative drug for the treatment of islet cell, cervical, testicular and adrenocortical cancers. It is also an immunosuppressant.

Doxorubicin is absorbed poorly and must be administered intravenously. The pharmacokinetics are multicompartmental. Distribution phases have half-lives of 12 minutes and 3.3 hr. The elimination half-life is about 30 hr. Forty to 50% is secreted into the bile. Most of the remainder is metabolized in the liver, partly to an active metabolite (doxorubicinol), but a few percent is excreted into the urine. In the presence of liver impairment, the dose should be reduced.

Appropriate doses are, intravenous, adult, 60 to 75 mg/m$^2$ at 21-day intervals or 25 to 30 mg/m$^2$ on each of 2 or 3 successive days repeated at 3- or 4-wk intervals or 20 mg/m$^2$ once a week. The lowest dose should be used in elderly patients, when there is prior bone-marrow depression caused by prior chemotherapy or neoplastic marrow invasion, or when the drug is combined with other myelopoietic suppressant drugs. The dose should be reduced by 50% if the serum bilirubin lies between 1.2 and 3 mg/dL and by 75% if above 3 mg/dL. The lifetime total dose should not exceed 550 mg/m$^2$ in patients with normal heart function and 400 mg/m$^2$ in persons having received mediastinal irradiation. Alternatively, 30 mg/m$^2$ on each of 3 consecutive days, repeated every 4 wk. Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

In the present invention the inventors have employed doxorubicin as an exemplary chemotherapeutic agent to synergistically enhance the antineoplastic effects of the agRNAs in the treatment of cancers. Those of skill in the art will be able to use the invention as exemplified potentiate the effects of doxorubicin in a range of different pre-cancer and cancers.

b. Daunorubicin

Daunorubicin hydrochloride, 5,12-Naphthacenedione, (8S-cis)-8-acetyl-10-[(3-amino-2,3,6-trideoxy-a-L-lyxo-hexanopyranosyl)oxy]-7,8,9,10-tetrahydro-6,8,11-trihydroxy-10-methoxy-, hydrochloride; also termed cerubidine and is available from Wyeth. Daunorubicin intercalates into DNA, blocks DAN-directed RNA polymerase and inhibits DNA synthesis. It can prevent cell division in doses that do not interfere with nucleic acid synthesis.

In combination with other drugs it is included in the first-choice chemotherapy of acute myelocytic leukemia in adults (for induction of remission), acute lymphocytic leukemia and the acute phase of chronic myelocytic leukemia. Oral absorption is poor, and it must be given intravenously. The half-life of distribution is 45 minutes and of elimination, about 19 hr. The half-life of its active metabolite, daunorubicinol, is about 27 hr. Daunorubicin is metabolized mostly in the liver and also secreted into the bile (ca 40%). Dosage must be reduced in liver or renal insufficiencies.

Suitable doses are (base equivalent), intravenous adult, younger than 60 yr. 45 mg/m$^2$/day (30 mg/m$^2$ for patients older than 60 yr.) for 1, 2 or 3 days every 3 or 4 wk or 0.8 mg/kg/day for 3 to 6 days every 3 or 4 wk; no more than 550 mg/m$^2$ should be given in a lifetime, except only 450 mg/m$^2$ if there has been chest irradiation; children, 25 mg/m$^2$ once a week unless the age is less than 2 yr. or the body surface less than 0.5 m, in which case the weight-based adult schedule is used. It is available in injectable dosage forms (base equivalent) 20 mg (as the base equivalent to 21.4 mg of the hydrochloride). Exemplary doses may be 10 mg/m$^2$, 20 mg/m$^2$, 30 mg/m$^2$, 50 mg/m$^2$, 100 mg/m$^2$, 150 mg/m$^2$, 175 mg/m$^2$, 200 mg/m$^2$, 225 mg/m$^2$, 250 mg/m$^2$, 275 mg/m$^2$, 300 mg/m$^2$, 350 mg/m$^2$, 400 mg/m$^2$, 425 mg/m$^2$, 450 mg/m$^2$, 475 mg/m$^2$, 500 mg/m$^2$. Of course, all of these dosages are exemplary, and any dosage in-between these points is also expected to be of use in the invention.

c. Mitomycin

Mitomycin (also known as mutamycin and/or mitomycin-C) is an antibiotic isolated from the broth of *Streptomyces caespitosus* which has been shown to have antitumor activity. The compound is heat stable, has a high melting point, and is freely soluble in organic solvents.

Mitomycin selectively inhibits the synthesis of deoxyribonucleic acid (DNA). The guanine and cytosine content of DNA correlates with the degree of mitomycin-induced cross-linking. At high concentrations of the drug, cellular RNA and protein synthesis are also suppressed.

In humans, mitomycin is rapidly cleared from the serum after intravenous administration. Time required to reduce the serum concentration by 50% after a 30 mg. bolus injection is 17 minutes. After injection of 30 mg, 20 mg, or 10 mg I.V., the maximal serum concentrations were 2.4 mg/ml, 1.7 mg/ml, and 0.52 mg/ml, respectively. Clearance is effected primarily by metabolism in the liver, but metabolism occurs in other tissues as well. The rate of clearance is inversely proportional to the maximal serum concentration because, it is thought, of saturation of the degradative pathways. Approximately 10% of a dose of mitomycin is excreted unchanged in the urine. Since metabolic pathways are saturated at relatively low doses, the percent of a dose excreted in urine increases with increasing dose. In children, excretion of intravenously administered mitomycin is similar.

d. Actinomycin D

Actinomycin D (Dactinomycin) [50-76-0]; $C_{62}H_{86}N_{12}O_{16}$ (1255.43) is an antineoplastic drug that inhibits DNA-dependent RNA polymerase. It is a component of first-choice combinations for treatment of choriocarcinoma, embryonal rhabdomyosarcoma, testicular tumor and Wilms' tumor. Tumors that fail to respond to systemic treatment sometimes respond to local perfusion. Dactinomycin potentiates radiotherapy. It is a secondary (efferent) immunosuppressive.

Actinomycin D is used in combination with primary surgery, radiotherapy, and other drugs, particularly vincristine and cyclophosphamide. Antineoplastic activity has also been noted in Ewing's tumor, Kaposi's sarcoma, and soft-tissue sarcomas. Dactinomycin can be effective in women with advanced cases of choriocarcinoma. It also produces consistent responses in combination with chlorambucil and methotrexate in patients with metastatic testicular carcinomas. A response may sometimes be observed in patients with Hodgkin's disease and non-Hodgkin's lymphomas. Dactinomycin has also been used to inhibit immunological responses, particularly the rejection of renal transplants.

Half of the dose is excreted intact into the bile and 10% into the urine; the half-life is about 36 hr. The drug does not pass the blood-brain barrier. Actinomycin D is supplied as a lyophilized powder (0/5 mg in each vial). The usual daily dose is 10 to 15 mg/kg; this is given intravenously for 5 days; if no manifestations of toxicity are encountered, additional courses may be given at intervals of 3 to 4 weeks. Daily injections of 100 to 400 mg have been given to children for 10 to 14 days; in other regimens, 3 to 6 mg/kg, for a total of 125 mg/kg, and weekly maintenance doses of 7.5 mg/kg have been used. Although it is safer to administer the drug into the tubing of an intravenous infusion, direct intravenous injections have been given, with the precaution of discarding the needle used to withdraw the drug from the vial in order to avoid subcutaneous reaction. Exemplary doses may be 100 mg/m², 150 mg/m², 175 mg/m², 200 mg/m², 225 mg/m², 250 mg/m², 275 mg/m², 300 mg/m², 350 mg/m², 400 mg/m², 425 mg/m², 450 mg/m², 475 mg/m², 500 mg/m². Of course, all of these dosages are exemplary, and any dosage in-between these points is also expected to be of use in the invention.

e. Bleomycin

Bleomycin is a mixture of cytotoxic glycopeptide antibiotics isolated from a strain of *Streptomyces verticillus*. Although the exact mechanism of action of bleomycin is unknown, available evidence would seem to indicate that the main mode of action is the inhibition of DNA synthesis with some evidence of lesser inhibition of RNA and protein synthesis.

In mice, high concentrations of bleomycin are found in the skin, lungs, kidneys, peritoneum, and lymphatics. Tumor cells of the skin and lungs have been found to have high concentrations of bleomycin in contrast to the low concentrations found in hematopoietic tissue. The low concentrations of bleomycin found in bone marrow may be related to high levels of bleomycin degradative enzymes found in that tissue.

In patients with a creatinine clearance of >35 ml per minute, the serum or plasma terminal elimination half-life of bleomycin is approximately 115 minutes. In patients with a creatinine clearance of <35 mL per minute, the plasma or serum terminal elimination half-life increases exponentially as the creatinine clearance decreases. In humans, 60% to 70% of an administered dose is recovered in the urine as active bleomycin. Bleomycin may be given by the intramuscular, intravenous, or subcutaneous routes. It is freely soluble in water.

Bleomycin should be considered a palliative treatment. It has been shown to be useful in the management of the following neoplasms either as a single agent or in proven combinations with other approved chemotherapeutic agents in squamous cell carcinoma such as head and neck (including mouth, tongue, tonsil, nasopharynx, oropharynx, sinus, palate, lip, buccal mucosa, gingiva, epiglottis, larynx), skin, penis, cervix, and vulva. It has also been used in the treatment of lymphomas and testicular carcinoma.

Because of the possibility of an anaphylactoid reaction, lymphoma patients should be treated with two units or less for the first two doses. If no acute reaction occurs, then the regular dosage schedule may be followed.

Improvement of Hodgkin's Disease and testicular tumors is prompt and noted within 2 weeks. If no improvement is seen by this time, improvement is unlikely. Squamous cell cancers respond more slowly, sometimes requiring as long as 3 weeks before any improvement is noted.

iv. Mitotic Inhibitors

Mitotic inhibitors include plant alkaloids and other natural agents that can inhibit either protein synthesis required for cell division or mitosis. They operate during a specific phase during the cell cycle. Mitotic inhibitors comprise docetaxel, etoposide (VP16), paclitaxel, taxol, taxotere, vinblastine, vincristine, and vinorelbine.

a. Etoposide (VP16)

VP16 is also known as etoposide and is used primarily for treatment of testicular tumors, in combination with bleomycin and cisplatin, and in combination with cisplatin for small-cell carcinoma of the lung. It is also active against non-Hodgkin's lymphomas, acute non-lymphocytic leukemia, carcinoma of the breast, and Kaposi's sarcoma associated with acquired immunodeficiency syndrome (AIDS).

VP16 is available as a solution (20 mg/ml) for intravenous administration and as 50-mg, liquid-filled capsules for oral use. For small-cell carcinoma of the lung, the intravenous dose (in combination therapy) is can be as much as 100 mg/m² or as little as 2 mg/m², routinely 35 mg/m², daily for 4 days, to 50 mg/m², daily for 5 days have also been used. When given orally, the dose should be doubled. Hence the doses for small cell lung carcinoma may be as high as 200-250 mg/m². The intravenous dose for testicular cancer (in combination therapy) is 50 to 100 mg/m² daily for 5 days, or 100 mg/m² on alternate days, for three doses. Cycles of therapy are usually repeated every 3 to 4 weeks. The drug should be administered slowly during a 30- to 60-minute infusion in order to avoid hypotension and bronchospasm, which are probably due to the solvents used in the formulation.

b. Taxol

Taxol is an antimitotic agent, isolated from the bark of the ash tree, *Taxus brevifolia*. It binds to tubulin (at a site distinct from that used by the vinca alkaloids) and promotes the assembly of microtubules. Taxol has activity against malignant melanoma and carcinoma of the ovary. Maximal doses are 30 mg/m$^2$ per day for 5 days or 210 to 250 mg/m$^2$ given once every 3 weeks. Of course, all of these dosages are exemplary, and any dosage in-between these points is also expected to be of use in the invention.

c. Vinblastine

Vinblastine is another example of a plant alkyloid that can be used in combination with agRNA for the treatment of cancer and precancer. When cells are incubated with vinblastine, dissolution of the microtubules occurs.

Unpredictable absorption has been reported after oral administration of vinblastine or vincristine. At the usual clinical doses the peak concentration of each drug in plasma is approximately 0.4 mM. Vinblastine and vincristine bind to plasma proteins. They are extensively concentrated in platelets and to a lesser extent in leukocytes and erythrocytes.

After intravenous injection, vinblastine has a multiphasic pattern of clearance from the plasma; after distribution, drug disappears from plasma with half-lives of approximately 1 and 20 hours. Vinblastine is metabolized in the liver to biologically activate derivative desacetylvinblastine. Approximately 15% of an administered dose is detected intact in the urine, and about 10% is recovered in the feces after biliary excretion. Doses should be reduced in patients with hepatic dysfunction. At least a 50% reduction in dosage is indicated if the concentration of bilirubin in plasma is greater than 3 mg/dl (about 50 mM).

Vinblastine sulfate is available in preparations for injection. The drug is given intravenously; special precautions must be taken against subcutaneous extravasation, since this may cause painful irritation and ulceration. The drug should not be injected into an extremity with impaired circulation. After a single dose of 0.3 mg/kg of body weight, myelosuppression reaches its maximum in 7 to 10 days. If a moderate level of leukopenia (approximately 3000 cells/mm$^3$) is not attained, the weekly dose may be increased gradually by increments of 0.05 mg/kg of body weight. In regimens designed to cure testicular cancer, vinblastine is used in doses of 0.3 mg/kg every 3 weeks irrespective of blood cell counts or toxicity.

The most important clinical use of vinblastine is with bleomycin and cisplatin in the curative therapy of metastatic testicular tumors. Beneficial responses have been reported in various lymphomas, particularly Hodgkin's disease, where significant improvement may be noted in 50 to 90% of cases. The effectiveness of vinblastine in a high proportion of lymphomas is not diminished when the disease is refractory to alkylating agents. It is also active in Kaposi's sarcoma, neuroblastoma, and Letterer-Siwe disease (histiocytosis X), as well as in carcinoma of the breast and choriocarcinoma in women.

Doses of vinblastine will be determined by the clinician according to the individual patients need. 0.1 to 0.3 mg/kg can be administered or 1.5 to 2 mg/m$^2$ can also be administered. Alternatively, 0.1 mg/m$^2$, 0.12 mg/m$^2$, 0.14 mg/m$^2$, 0.15 mg/m$^2$, 0.2 mg/m$^2$, 0.25 mg/m$^2$, 0.5 mg/m$^2$, 1.0 mg/m$^2$, 1.2 mg/m$^2$, 1.4 mg/m$^2$, 1.5 mg/m$^2$, 2.0 mg/m$^2$, 2.5 mg/m$^2$, 5.0 mg/m$^2$, 6 mg/m$^2$, 8 mg/m$^2$, 9 mg/m$^2$, 10 mg/m$^2$, 20 mg/m$^2$, can be given. Of course, all of these dosages are exemplary, and any dosage in-between these points is also expected to be of use in the invention.

d. Vincristine

Vincristine blocks mitosis and produces metaphase arrest. It seems likely that most of the biological activities of this drug can be explained by its ability to bind specifically to tubulin and to block the ability of protein to polymerize into microtubules. Through disruption of the microtubules of the mitotic apparatus, cell division is arrested in metaphase. The inability to segregate chromosomes correctly during mitosis presumably leads to cell death.

The relatively low toxicity of vincristine for normal marrow cells and epithelial cells make this agent unusual among anti-neoplastic drugs, and it is often included in combination with other myelosuppressive agents.

Unpredictable absorption has been reported after oral administration of vinblastine or vincristine. At the usual clinical doses the peak concentration of each drug in plasma is approximately 0.4 mM.

Vinblastine and vincristine bind to plasma proteins. They are extensively concentrated in platelets and to a lesser extent in leukocytes and erythrocytes.

Vincristine has a multiphasic pattern of clearance from the plasma; the terminal half-life is about 24 hours. The drug is metabolized in the liver, but no biologically active derivatives have been identified. Doses should be reduced in patients with hepatic dysfunction. At least a 50% reduction in dosage is indicated if the concentration of bilirubin in plasma is greater than 3 mg/dl (about 50 mM).

Vincristine sulfate is available as a solution (1 mg/ml) for intravenous injection. Vincristine used together with corticosteroids is presently the treatment of choice to induce remissions in childhood leukemia; the optimal dosages for these drugs appear to be vincristine, intravenously, 2 mg/m$^2$ of body-surface area, weekly, and prednisone, orally, 40 mg/m$^2$, daily. Adult patients with Hodgkin's disease or non-Hodgkin's lymphomas usually receive vincristine as a part of a complex protocol. When used in the MOPP regimen, the recommended dose of vincristine is 1.4 mg/m$^2$. High doses of vincristine seem to be tolerated better by children with leukemia than by adults, who may experience sever neurological toxicity. Administration of the drug more frequently than every 7 days or at higher doses seems to increase the toxic manifestations without proportional improvement in the response rate. Precautions should also be used to avoid extravasation during intravenous administration of vincristine. Vincristine (and vinblastine) can be infused into the arterial blood supply of tumors in doses several times larger than those that can be administered intravenously with comparable toxicity.

Vincristine has been effective in Hodgkin's disease and other lymphomas. Although it appears to be somewhat less beneficial than vinblastine when used alone in Hodgkin's disease, when used with mechlorethamine, prednisone, and procarbazine (the so-called MOPP regimen), it is the preferred treatment for the advanced stages (III and IV) of this disease. In non-Hodgkin's lymphomas, vincristine is an important agent, particularly when used with cyclophosphamide, bleomycin, doxorubicin, and prednisone. Vincristine is more useful than vinblastine in lymphocytic leukemia. Beneficial response have been reported in patients with a variety of other neoplasms, particularly Wilms' tumor, neuroblastoma, brain tumors, rhabdomyosarcoma, and carcinomas of the breast, bladder, and the male and female reproductive systems.

Doses of vincristine for use will be determined by the clinician according to the individual patients need. 0.01 to 0.03 mg/kg or 0.4 to 1.4 mg/m$^2$ can be administered or 1.5 to 2 mg/m$^2$ can also be administered. Alternatively 0.02 mg/m$^2$, 0.05 mg/m², 0.06 mg/m², 0.07 mg/m², 0.08 mg/m², 0.1 mg/m², 0.12 mg/m², 0.14 mg/m², 0.15 mg/m², 0.2 mg/m², 0.25 mg/m² can be given as a constant intravenous infusion. Of course, all of these dosages are exemplary, and any dosage in-between these points is also expected to be of use in the invention.

e. Camptothecin

Camptothecin is an alkaloid derived from the Chinese tree *Camptotheca acuminata* Decne. Camptothecin and its derivatives are unique in their ability to inhibit DNA Topoisomerase by stabilizing a covalent reaction intermediate, termed "the cleavable complex," which ultimately causes tumor cell death. It is widely believed that camptothecin analogs exhibited remarkable anti-tumor and anti-leukemia activity. Application of camptothecin in clinic is limited due to serious side effects and poor water-solubility. At present, some camptothecin analogs (topotecan; irinotecan), either synthetic or semi-synthetic, have been applied to cancer therapy and have shown satisfactory clinical effects. The molecular formula for camptothecin is $C_{20}H_{16}N_2O_4$, with a molecular weight of 348.36. It is provided as a yellow powder, and may be solubilized to a clear yellow solution at 50 mg/ml in DMSO 1N sodium hydroxide. It is stable for at least two years if stored at 2-8° X in a dry, airtight, light-resistant environment.

v. Nitrosureas

Nitrosureas, like alkylating agents, inhibit DNA repair proteins. They are used to treat non-Hodgkin's lymphomas, multiple myeloma, malignant melanoma, in addition to brain tumors. Examples include carmustine and lomustine.

a. Carmustine

Carmustine (sterile carmustine) is one of the nitrosoureas used in the treatment of certain neoplastic diseases. It is 1,3bis(2-chloroethyl)-1-nitrosourea. It is lyophilized pale yellow flakes or congealed mass with a molecular weight of 214.06. It is highly soluble in alcohol and lipids, and poorly soluble in water. Carmustine is administered by intravenous infusion after reconstitution as recommended. Sterile carmustine is commonly available in 100 mg single dose vials of lyophilized material.

Although it is generally agreed that carmustine alkylates DNA and RNA, it is not cross resistant with other alkylators. As with other nitrosoureas, it may also inhibit several key enzymatic processes by carbamoylation of amino acids in proteins.

Carmustine is indicated as palliative therapy as a single agent or in established combination therapy with other approved chemotherapeutic agents in brain tumors such as glioblastoma, brainstem glioma, medullobladyoma, astrocytoma, ependymoma, and metastatic brain tumors. Also it has been used in combination with prednisone to treat multiple myeloma. Carmustine has proved useful, in the treatment of Hodgkin's Disease and in non-Hodgkin's lymphomas, as secondary therapy in combination with other approved drugs in patients who relapse while being treated with primary therapy, or who fail to respond to primary therapy.

The recommended dose of carmustine as a single agent in previously untreated patients is 150 to 200 mg/m² intravenously every 6 weeks. This may be given as a single dose or divided into daily injections such as 75 to 100 mg/m² on 2 successive days. When carmustine is used in combination with other myelosuppressive drugs or in patients in whom bone marrow reserve is depleted, the doses should be adjusted accordingly. Doses subsequent to the initial dose should be adjusted according to the hematologic response of the patient to the preceding dose. It is of course understood that other doses may be used in the present invention for example 10 mg/m², 20 mg/m², 30 mg/m² 40 mg/m² 50 mg/m² 60 mg/m² 70 mg/m² 80 mg/m² 90 mg/m² 100 mg/m². The skilled artisan is directed to, "Remington's Pharmaceutical Sciences" 15th Edition, chapter 61. Some variation in dosage will necessarily occur depending on the condition of the subject being treated. The person responsible for administration will, in any event, determine the appropriate dose for the individual subject.

b. Lomustine

Lomustine is one of the nitrosoureas used in the treatment of certain neoplastic diseases. It is 1-(2-chloro-ethyl)-3-cyclohexyl-1 nitrosourea. It is a yellow powder with the empirical formula of $C_9H_{16}ClN_3O_2$ and a molecular weight of 233.71. Lomustine is soluble in 10% ethanol (0.05 mg per mL) and in absolute alcohol (70 mg per mL). Lomustine is relatively insoluble in water (<0.05 mg per mL). It is relatively unionized at a physiological pH. Inactive ingredients in lomustine capsules are magnesium stearate and mannitol.

Although it is generally agreed that lomustine alkylates DNA and RNA, it is not cross resistant with other alkylators. As with other nitrosoureas, it may also inhibit several key enzymatic processes by carbamoylation of amino acids in proteins.

Lomustine may be given orally. Following oral administration of radioactive lomustine at doses ranging from 30 mg/m² to 100 mg/m², about half of the radioactivity given was excreted in the form of degradation products within 24 hours. The serum half-life of the metabolites ranges from 16 hours to 2 days. Tissue levels are comparable to plasma levels at 15 minutes after intravenous administration.

Lomustine has been shown to be useful as a single agent in addition to other treatment modalities, or in established combination therapy with other approved chemotherapeutic agents in both primary and metastatic brain tumors, in patients who have already received appropriate surgical and/or radiotherapeutic procedures. It has also proved effective in secondary therapy against Hodgkin's Disease in combination with other approved drugs in patients who relapse while being treated with primary therapy, or who fail to respond to primary therapy.

The recommended dose of lomustine in adults and children as a single agent in previously untreated patients is 130 mg/m² as a single oral dose every 6 weeks. In individuals with compromised bone marrow function, the dose should be reduced to 100 mg/m² every 6 weeks. When lomustine is used in combination with other myelosuppressive drugs, the doses should be adjusted accordingly. It is understood that other doses may be used for example, 20 mg/m² 30 mg/m², 40 mg/m², 50 mg/m², 60 mg/m², 70 mg/m², 80 mg/m², 90 mg/m², 100 mg/m², 120 mg/m² or any doses between these figures as determined by the clinician to be necessary for the individual being treated.

vi. Other Agents

Other agents that may be used include Avastin, Iressa, Erbitux, Velcade, and. Gleevec. In addition, growth factor inhibitors and small molecule kinase inhibitors have utility in the present invention as well. All therapies described in Cancer: Principles and Practice of Oncology Single Volume (2001), are hereby incorporated by reference. The following additional therapies are encompassed, as well.

2. Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with agRNA inhibitors. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Tumor Necrosis Factor is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anti-cancer activity.

3. Hormonal Therapy

The use of sex hormones according to the methods described herein in the treatment of cancer. While the methods described herein are not limited to the treatment of a specific cancer, this use of hormones has benefits with respect to cancers of the breast, prostate, and endometrial (lining of the uterus). Examples of these hormones are estrogens, antiestrogens, progesterones, and androgens.

Corticosteroid hormones are useful in treating some types of cancer (lymphoma, leukemias, and multiple myeloma). Corticosteroid hormones can increase the effectiveness of other chemotherapy agents, and consequently, they are frequently used in combination treatments. Prednisone and dexamethasone are examples of corticosteroid hormones.

4. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively).

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area from being destroyed. This means that the risk of the cancer coming back in the future may be higher with these specialized radiotherapy techniques. Stereotactic radiotherapy is used to treat brain tumors. This technique directs the radiotherapy from many different angles so that the dose going to the tumor is very high and the dose affecting surrounding healthy tissue is very low. Before treatment, several scans are analyzed by computers to ensure that the radiotherapy is precisely targeted, and the patient's head is held still in a specially made frame while receiving radiotherapy. Several doses are given.

Stereotactic radio-surgery (gamma knife) for brain tumors does not use a knife, but very precisely targeted beams of gamma radiotherapy from hundreds of different angles. Only one session of radiotherapy, taking about four to five hours, is needed. For this treatment you will have a specially made metal frame attached to your head. Then several scans and x-rays are carried out to find the precise area where the treatment is needed. During the radiotherapy, the patient lies with their head in a large helmet, which has hundreds of holes in it to allow the radiotherapy beams through.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

5. Subsequent Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Upon excision of part of all of cancerous cells, tissue, or tumor, a cavity may be formed in the body. Treatment using a anti-p53 agRNA may be accomplished by perfusion, direct injection or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

6. Gene Therapy

In another embodiment, the secondary treatment is a gene therapy. Delivery of a vector encoding a therapeutic gene in conjunction with an agRNA may be utilized. A variety of gene therapy agents are encompassed within this embodiment, some of which are described below.

i. Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor. In one embodiment of the present invention, it is contemplated that anti-sense mRNA directed to a particular inducer of cellular proliferation is used to prevent expression of the inducer of cellular proliferation.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

ii. Tumor Suppressors and Inhibitors of Cellular Proliferation

The tumor suppressor oncogenes function to inhibit excessive cellular proliferation. The inactivation of these genes destroys their inhibitory activity, resulting in unregulated proliferation. The tumor suppressors Rb, p16, MDA-7, PTEN and C-CAM are specifically contemplated.

One particular mode of administration that can be used in conjunction with surgery is treatment of an operative tumor bed. Thus, in either the primary gene therapy treatment, or in a subsequent treatment, one may perfuse the resected tumor bed with the vector during surgery, and following surgery, optionally by inserting a catheter into the surgery site.

iii. Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

V. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The inventors have demonstrated that agRNAs are potent inhibitors of transcription in human cancer cells (Janowski et al., 2005; Janowski et al., 2006). In their lab, they have focused on agRNAs that target oncogenes and tumor suppressor genes. Unexpectedly, they discovered that agRNAs directed against the promoter of the p53 tumor suppressor gene not only reduced full-length p53 expression, but also increased expression of an alternatively spliced (shorter) form of p53 protein. This altered expression profile resulted in dramatic tumor cell kill (FIGS. 1A-B).

The inventors hypothesize that agRNAs targeting full-length, mutant p53 in cancer cells will restores wild-type p53 function by reducing expression of dominant-negative, full-length isoforms of p53, as well as increasing the expression of Δp53 as well as other isoforms that excise portions of the p53 DNA binding domain. This agRNA restored function leads to tumor cell death in tumor cells with a p53 missense mutation, but has no effect on normal cells with wild-type p53.

Figure 2:
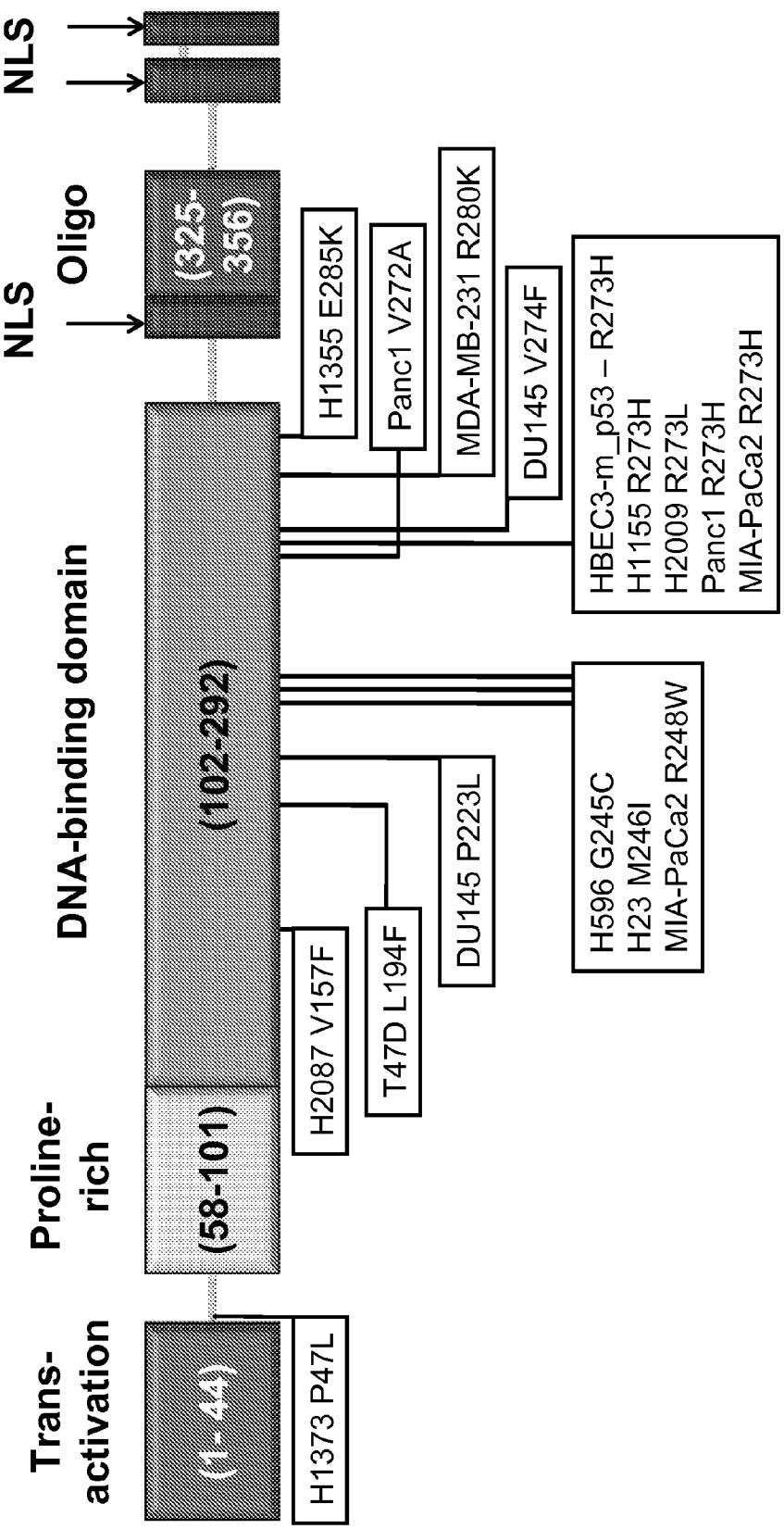
FIG. 2: Mutation Spectra for Cell Lines.
Figure 3A:
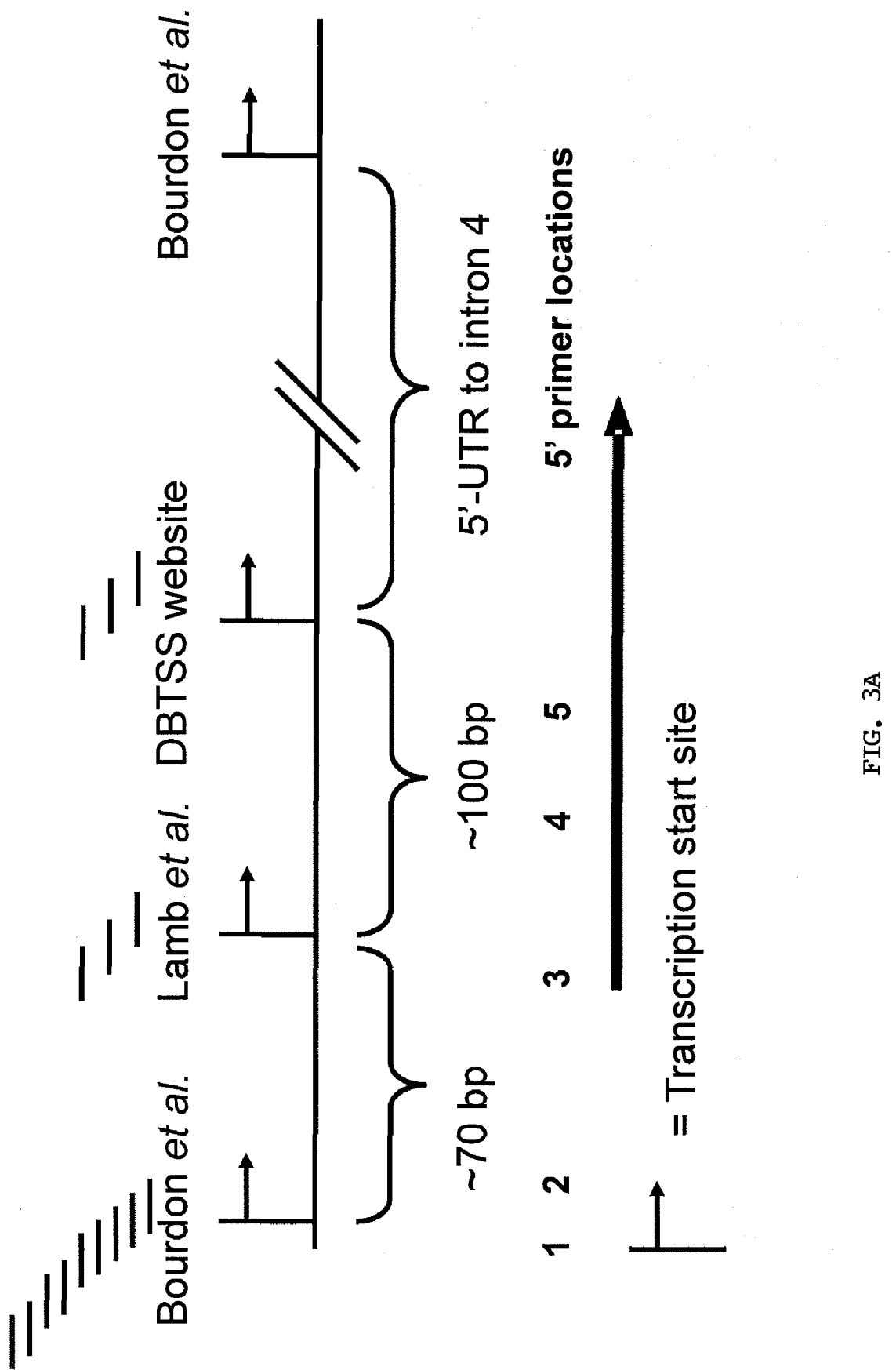

To test this hypothesis, the inventors have assessed the effect of p53 agRNAs against a variety of cell lines (N>25) including those derived from lung, breast, prostate, colon, pancreatic, and bone cancers as well as a series of recently developed immortalized bronchial epithelial cells (Table 2). These different cell lines include many with different point mutations within the DNA binding domain, several that have homozygous deletions in the p53 locus, as well as several with wild-type p53 (FIG. 2).

the cell lines utilized in this study, they first employed 5'-RACE strategy. The data show that the predominant site used in MCF-7 and T47D correspond to the classical transcription start site first characterized by Crawford and Lamb (1984). To further examine whether other cell lines used this site, the inventors performed RT-PCR using primers targeting various sites in the 5' region of the p53 locus (FIGS. 3A & 3C). They found that several cell lines had transcripts present 5' to the Crawford and Lamb (1984), but none had any corresponding to the most 5' site recently described in Bourdan et al. (2005). Based on these data, the inventors designed 21-mer duplex RNAs targeting this most 5' TSS site beginning with the −7 position and moving 5' through −31 relative to the TSS (FIG. 3A; Table 1).

Figure 4:
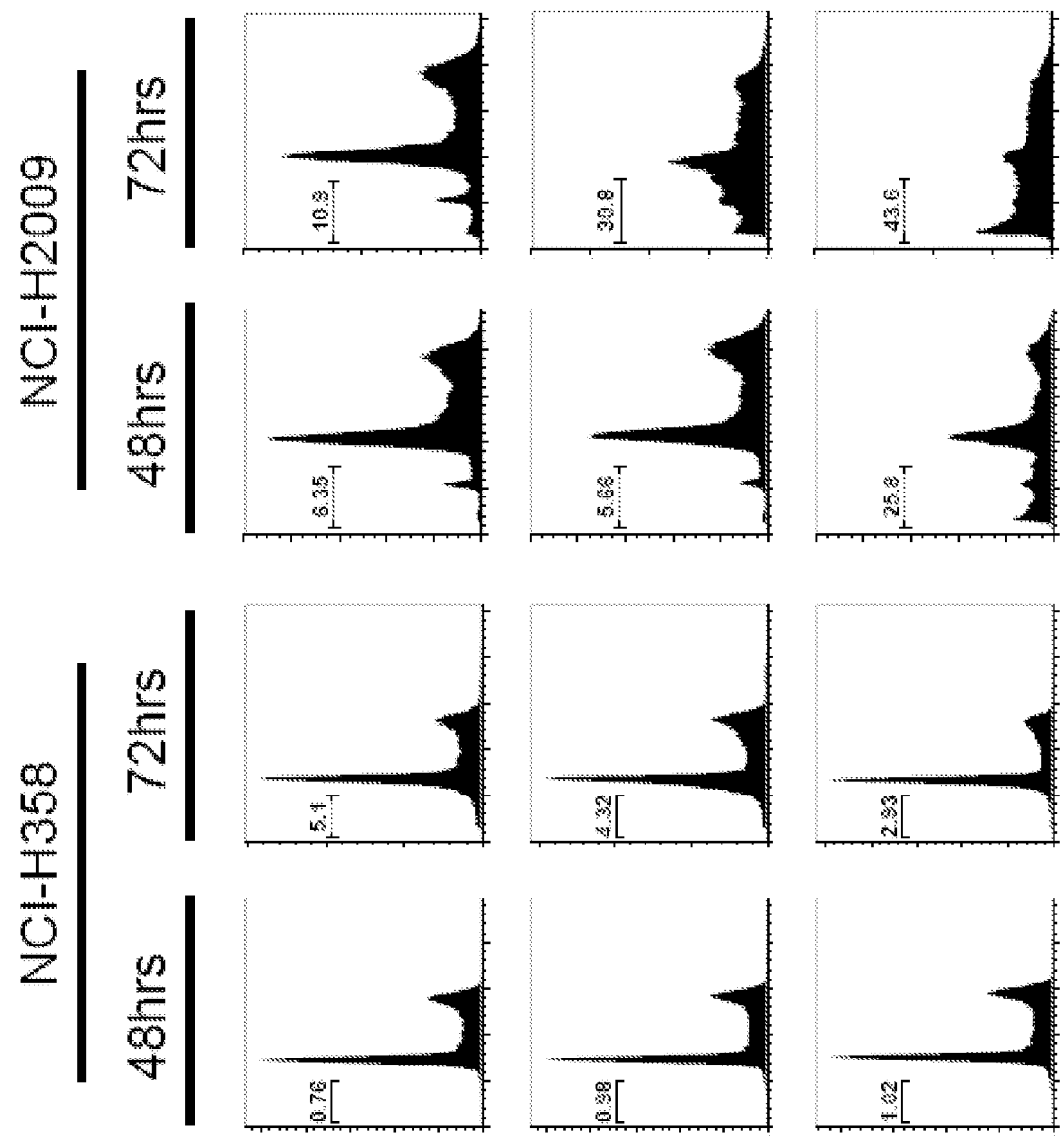
FIG. 4: Cell Cycle Profile of Cells with Mutant p53 and Homozygously Deleted p53 After Treatment with 25 mM agRNA after 48 and 72 h.

To determine whether agRNA$_{sp53}$ altered the cell cycle of mutant cell lines, the inventors looked at DNA content using propidium iodide (FIG. 4). Cells with homozygously deleted

TABLE 2

Cells Lines used for p53 agRNA Studies

| Cell Line | Tissue | Origin | p53 Status | Phenotype-Cytotoxicity | Promoter Profile | FACS | MTS | Colony Formation | DAPI Counting |
|---|---|---|---|---|---|---|---|---|---|
| HBEC3 | Lung | Bronchus | Wild Type | N | N | N | Y | Y | N |
| HBEC3-mutp53 | Lung | Bronchus | Het H273R | N | Y | N | Y | N | N |
| HBEC3-shp53 | Lung | Bronchus | Wild Type | N | N | N | Y | N | N |
| HBEC30 | Lung | Bronchus | Wild Type | N | N | Y | N | N | N |
| HCC4017 | Lung | Peripheral Lung | Wild Type | N | N | Y | N | N | N |
| A549 | Lung | Peripheral Lung | Wild Type | N | N | Y | Y | Y | Y |
| H513 | Lung | Plural Effusion | Wild Type | N | N | Y | N | N | N |
| H1355 | Lung | Plural Effusion | E285K | Y | Y | N | Y | N | N |
| H2009 | Lung | Lymph Node | R273L | Y | Y | Y | Y | Y | Y |
| H1155 | Lung | Lymph Node | R273H | Y | N | N | N | N | N |
| H1819 | Lung | Lymph Node | ? | Y | N | Y | N | N | N |
| H2087 | Lung | Lymph Node | V157F | Y | N | N | N | Y | N |
| H596 | Lung | ? | G245C | Y | N | Y | N | N | N |
| H23 | Lung | ? | M2461 | Y | N | Y | N | N | N |
| H1299 | Lung | Plural Effusion | Intragenic deletion | Y* | Y | Y | Y | Y | Y |
| H358 | Lung | Peripheral Lung | null | N | Y | Y | Y | Y | Y |
| HCC827 | Lung | Peripheral Lung | ? | N | N | Y | N | N | N |
| SAOS-2 | Bone | | null | ? | N | N | N | N | N |
| Hs766 | Pancreas | Pancreas | exonic inversion | ? | N | N | N | N | N |
| Panc-1 | Pancreas | duct | V272A, R273H | Y | Y | Y | Y | Y | Y |
| MIA-PaCa 2 | Pancreas | Pancreas | R248W, R273H | Y | Y | N | Y | Y | N |
| T47D | Breast | Plural Effusion | L194F | Y | Y | Y | Y | N | N |
| MDA-MB-231 | Breast | Plural Effusion | R280K | Y | Y | Y | Y | Y | Y |
| MCF7 | Breast | Plural Effusion | Wild Type | N | Y | N | N | N | N |
| DU145 | Prostate | Brain Met | P223L, V274F | Y | Y | N | N | N | N |

The inventors tested a broad range of duplex RNAs corresponding to the three upstream promoters of p53 (FIG. 3A, Table 1). To evaluate whether agRNAs targeted to the p53 promoter targeted any identifiable processed RNA species in the p53 are unaffected by agRNA N9 and N27 after either 48 or 72 hrs, whereas cells with mutant p53 have undergone significant alterations in DNA content consistent with the induction of cell death. Importantly, this phenotype, as exhibited by the differences in sub-G0 cells, depends on both the time after transfection and the sequence of the oligo. A longer incubation period leads to an increase in dead cells, and N27 is more potent than N9 in H2009 cells. Neither duplex has any effect in H358. Interestingly, there did not seem to be an specific effect on any part of the cell cycle in H2009 cells, (a similar profile was observed in other mutant p53 cells), suggesting that other factors besides induction of Δp53 likely play an important part in this phenotype.

Figure 5A:
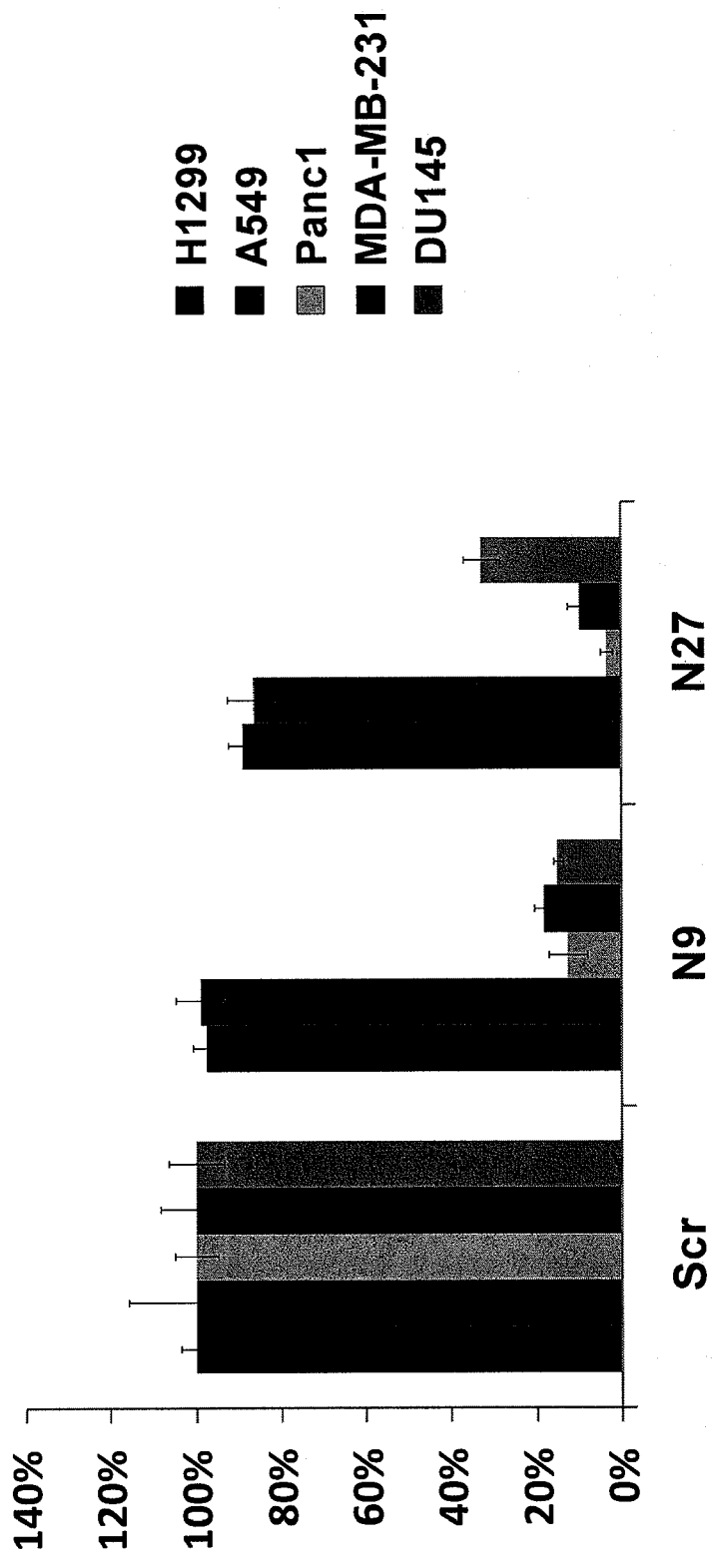
FIGS. 5A-B: DAPI/PI Staining in Indicated Cell Lines after Treatment with 25 nM agRNAs.

The inventors examined the effects of agRNA$_{p53}$ in more detail first using a simple cell counting strategy after short term transfection. In this assay, cells were plated at 10000 cells per chamber in 4-well chamber slides and transfected with oligos 24 hrs later. Forty-eight hrs after transfection, cells were incubated with propidium iodide for 2 minutes, washed 3 times with cold PBS, and then fixed in formalin. Cells were then mounted using vector shield and visualized separately in the red and blue channels. Cells with only DAPI staining were considered viable and those with both propidim iodide and DAPI were considered apoptotic. The data show that cells that are null or have wild-type p53 show no response to control scrambled duplex RNAs, N9, or N27. However, cells with mutant p53 are exquisitely sensitive to low dose treatment (FIG. 5A).

Figure 5B:
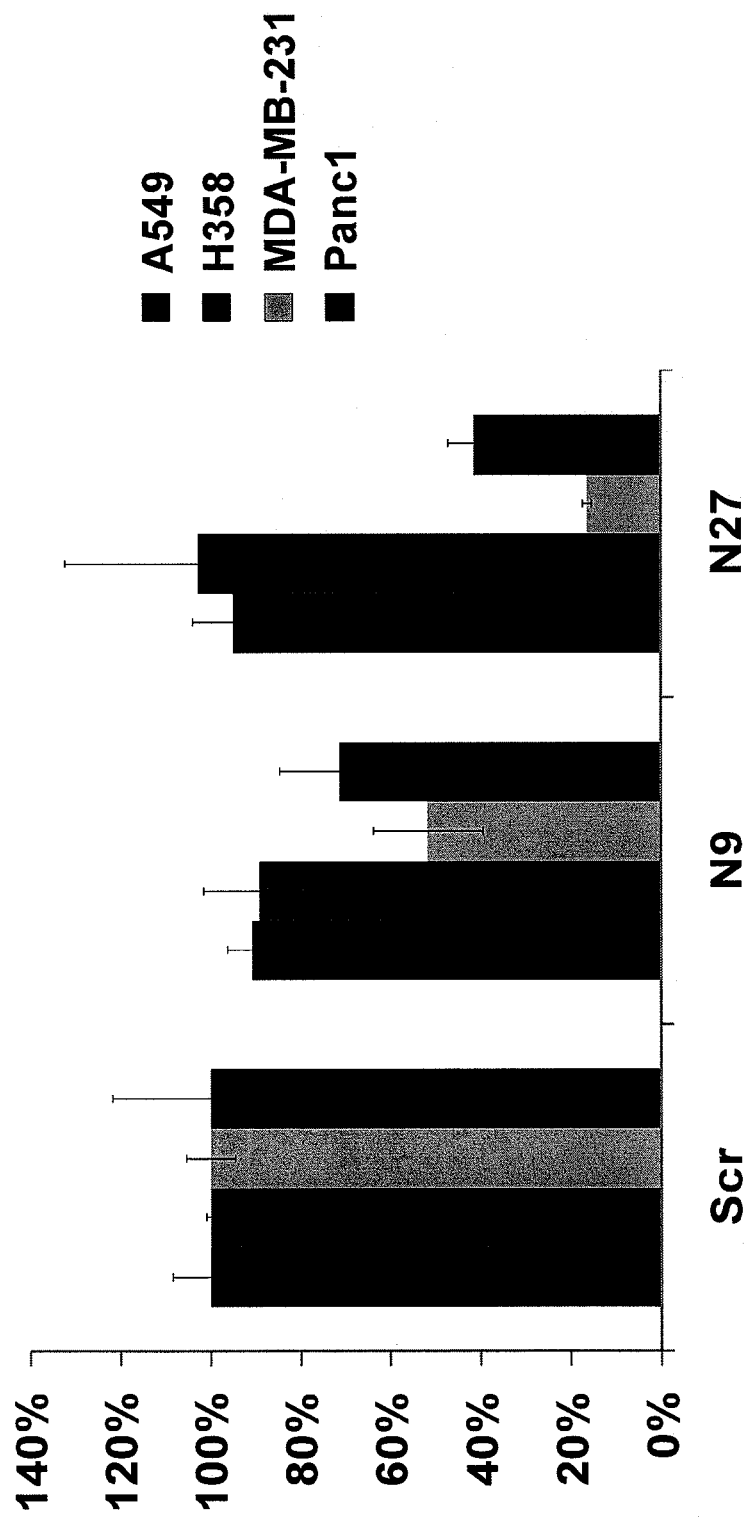

Transient transfection of duplex RNAs often results in non-specific effects mediated by an acute interferon response. To exclude the possibility that agRNAs induce an interferon response and to determine whether agRNAs inhibit colony formation in a longer term assay, the inventors transfected a series of cell lines with control and targeted RNAs and then harvested the cells the next day for re-plating or RNA extraction. They looked for induction of interferon inducible genes by QPCR and found no change in either OAS2 or INF-I1. Similar to the short term assay, cells that are null or have wild-type p53 show no response to control scrambled duplex RNAs, N9, or N27. However, cells with mutant p53 exhibit significantly reduced colony forming ability (FIGS. 5B & 5C).

Figure 6A:
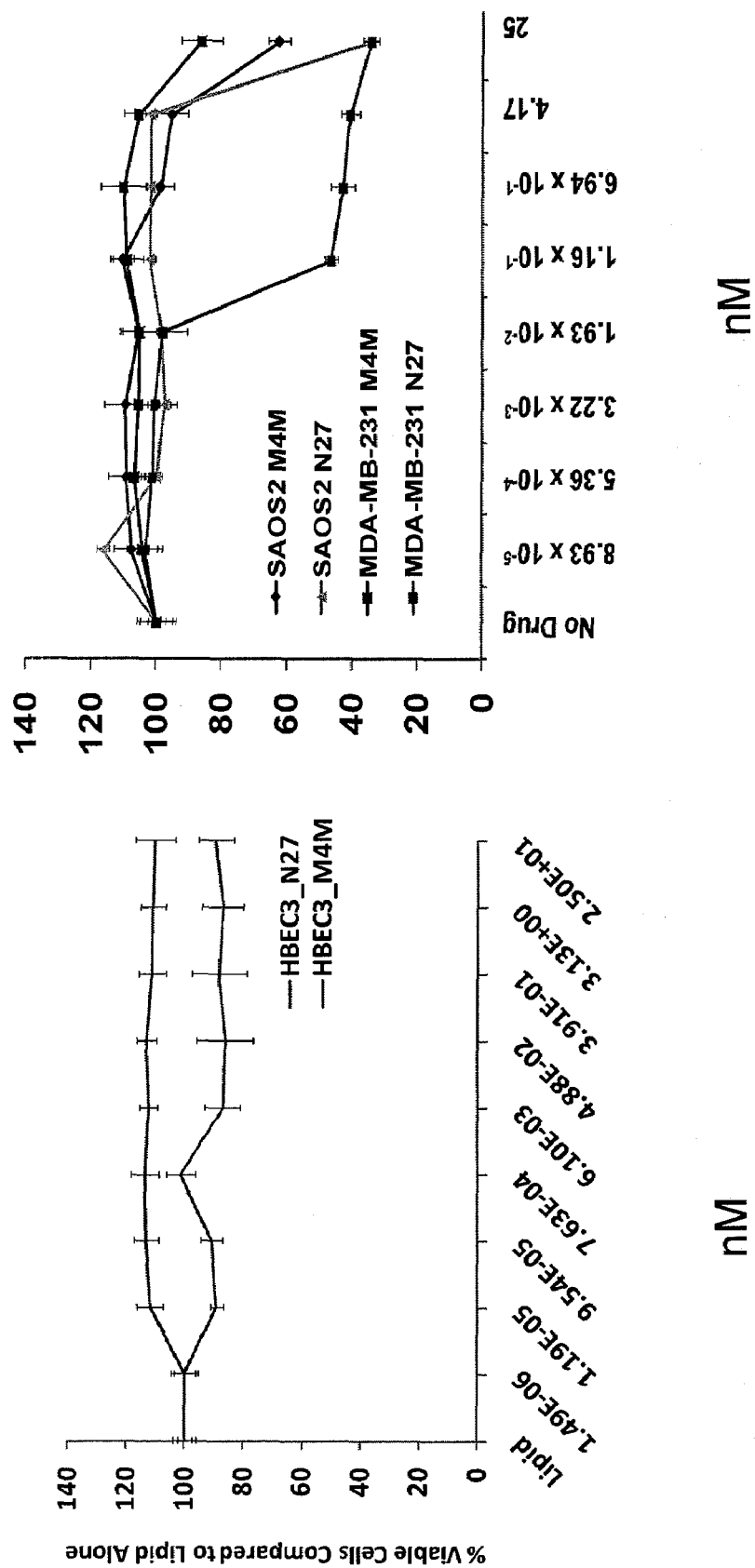
FIGS. 6A-B: Titration of agRNAs in Various Cell Types.
Figure 6B:
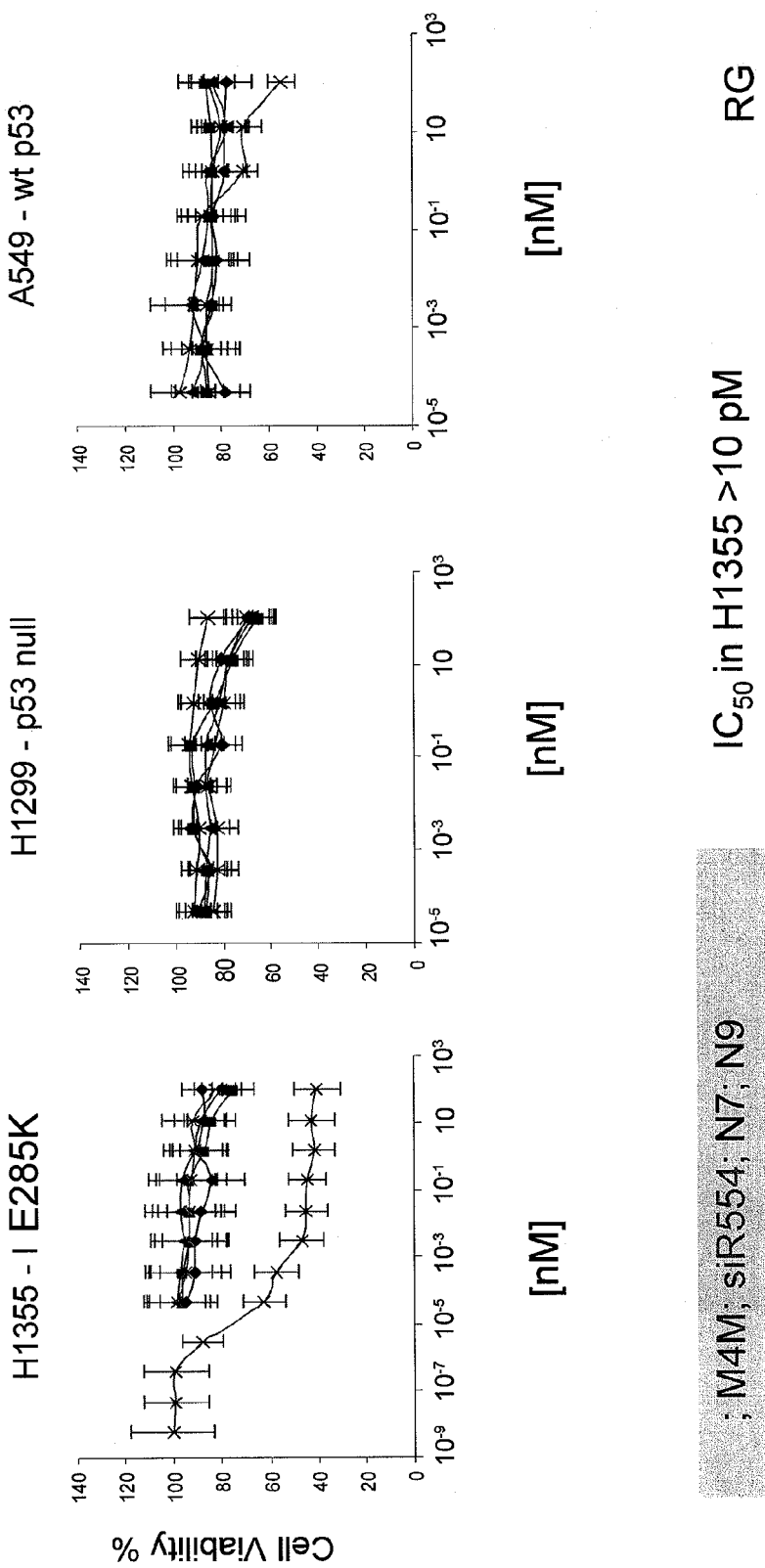
Figure 6C:
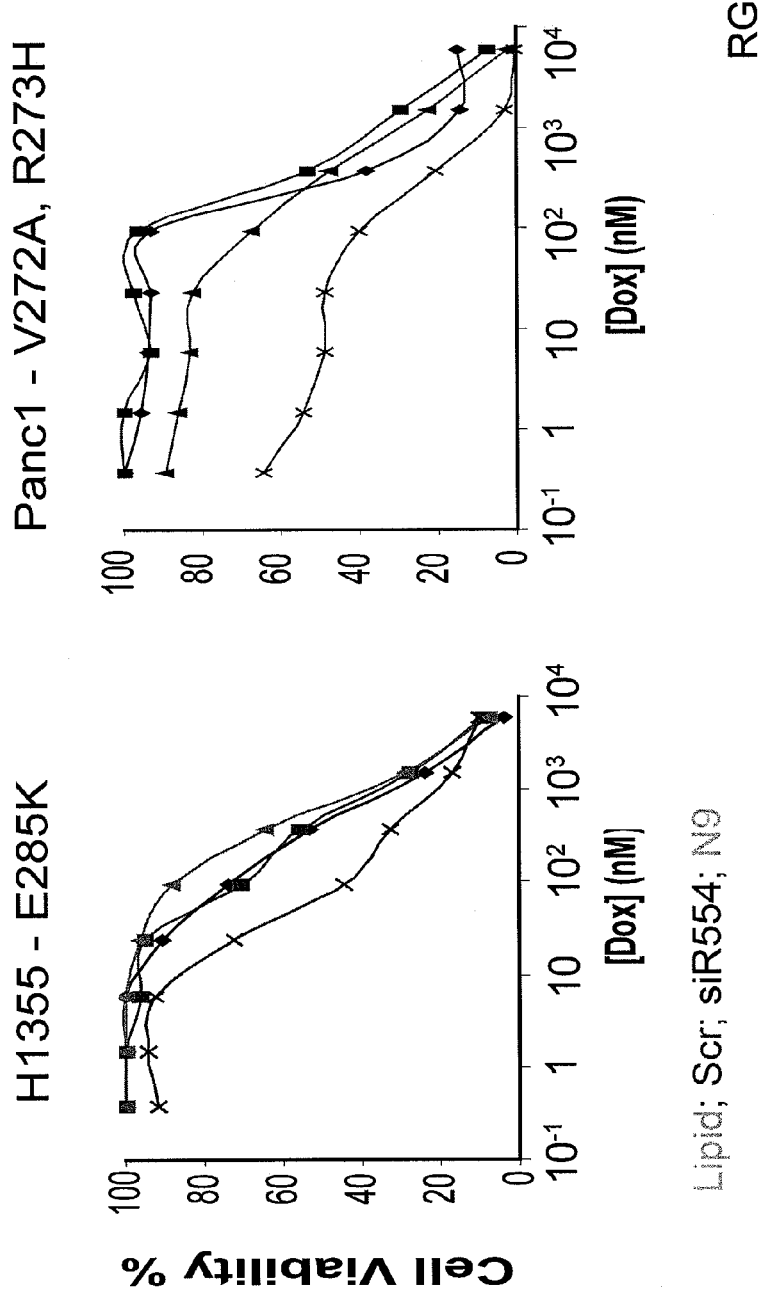
FIG. 6C: p53 agRNAs but not siR554 Sensitize Mutant p53 Cells to Dox. N9 was used at 100 pM; other oligos were used at 100 nM.

In an effort to determine the IC$_{50}$ values for some of the most potent oligonucleotides, the inventors used a standard 96-well microtiter plate cytotoxicity assay coupled with the reverse transfection method. Cancer cells with point mutations in the p53 DNA binding domain are acutely sensitive (low picomolar) to agRNAs targeting the upstream promoter of p53, whereas cells that are null for p53 (H1299) or have wild-type p53 (A549) are unaffected by agRNA treatment (FIG. 6A). In addition, the inventors evaluated HBEC cells (which are models of normal lung bronchial cells with wild-type p53) and an osteosarcoma cell line with homozygously deleted p53 for their response to N27 and found that that normal cells or cells without point mutations in p53 are unaffected by agRNA treatment, whereas breast cancer cells with point mutations in p53 are very sensitive to this treatment (FIG. 6B). Due to the unexpectedly high potency of these agRNAs (IC$_{50}$~low picomolar), the inventors have had three different investigators in two different labs using two different sources of oligonucleotide as well as different transfection protocols, repeat these experiments with similar results.

p53 is the sentinel responder to acute DNA damage (Vogelstein et al., 2000). Indeed, cells with point mutations in the p53 DNA binding domain are often resistant to chemotherapeutic agents that target DNA. The inventors examined whether agRNAs that target the p53 promoter might sensitize chemotherapy resistant lung cancer cells to DNA damaging agents. The data show that low dose (100 pM) of agRNA are sufficient to shift the IC$_{50}$ of doxorubicin more than 100-fold (FIG. 6C), whereas siRNAs targeting the p53 transcript have no effect of the IC$_{50}$ of doxorubicin.

To further demonstrate the specificity of the agRNAs discussed above, the inventors introduced mutant p53 (R273H) into H2009 cells. H2009 cells already express another mutant form of p53 (R273L) from its endogenous locus. The idea behind this experiment is to establish whether over-expression of mutant p53 can protect cells from the effects of agRNAs targeted to the endogenous promoter. The ectopic form of p53 is driven by a CMV promoter so the expectation is that expression of the mutant ectopic p53 will be unaffected by transfection of agRNA$_{p53}$. After selecting for zeocin resistance in virally infected H2009 cells, the inventors established several subclones cell lines. They compared the effects of N27 compared to control oligos by MTS assay (FIGS. 7A-C). The data show that stable expression of mutant p53 protects cells formally sensitive to N27. For comparison, vector transfected H2009 has an IC$_{50}$ of 50 pM, whereas neither H2009 mutant p53 Clone 1 or Clone 5 showed any response to N27.

To verify the results of the short term microtiter assay, the inventors performed liquid colony formation assays using the parental cell line (untransfected) the vector control (LacZ), and H2009 cells transfected with mutant p53. FIGS. 7A-D shows that both the parental cell line and the vector control cells were significantly inhibited by both N9 and N27, whereas there was a slight inhibition of the mutant p53 expressing H2009 cells. This small effect in the mutant p53 expressing H2009 cells probably results from the variable expression of the ectopic protein that is frequently observed in a population of transfected cells.

To examine the effects of N27 in an in vivo model of breast cancer, the inventors performed a pilot experiment in 6 mice (3 control, 3 treatment) using an established orthotopic breast model. Orthotopic breast tumors were established in female athymic nu/nu mice (NCl) using a small incision in the right flank of the animal whereupon the mammary fat pad visualized. MDA-MB-231 cells ($2.5\times10^6$ in 50 µl) were injected into the fat pad under direct visualization and the incision closed with a 5-0 prolene suture. Animals were monitored postoperatively and tumor volumes were assessed using calipers twice weekly. Volumes were calculated using the formula ($D*d_2*0.52$), where D is the largest diameter and d is the shortest. At sacrifice, the tumor was harvested and fixed in formalin for histologic analysis.

Treatment groups consisted of either a control lipid or N27 in lipid. In the mammary fat pad model, 230 picomoles of oligo was complexed in a 2:1 ratio with cationic lipid in 10 µl and administered into the tumor via a 30 gauge needle. Animals were sacrificed 3 days after treatment.

Figure 8:
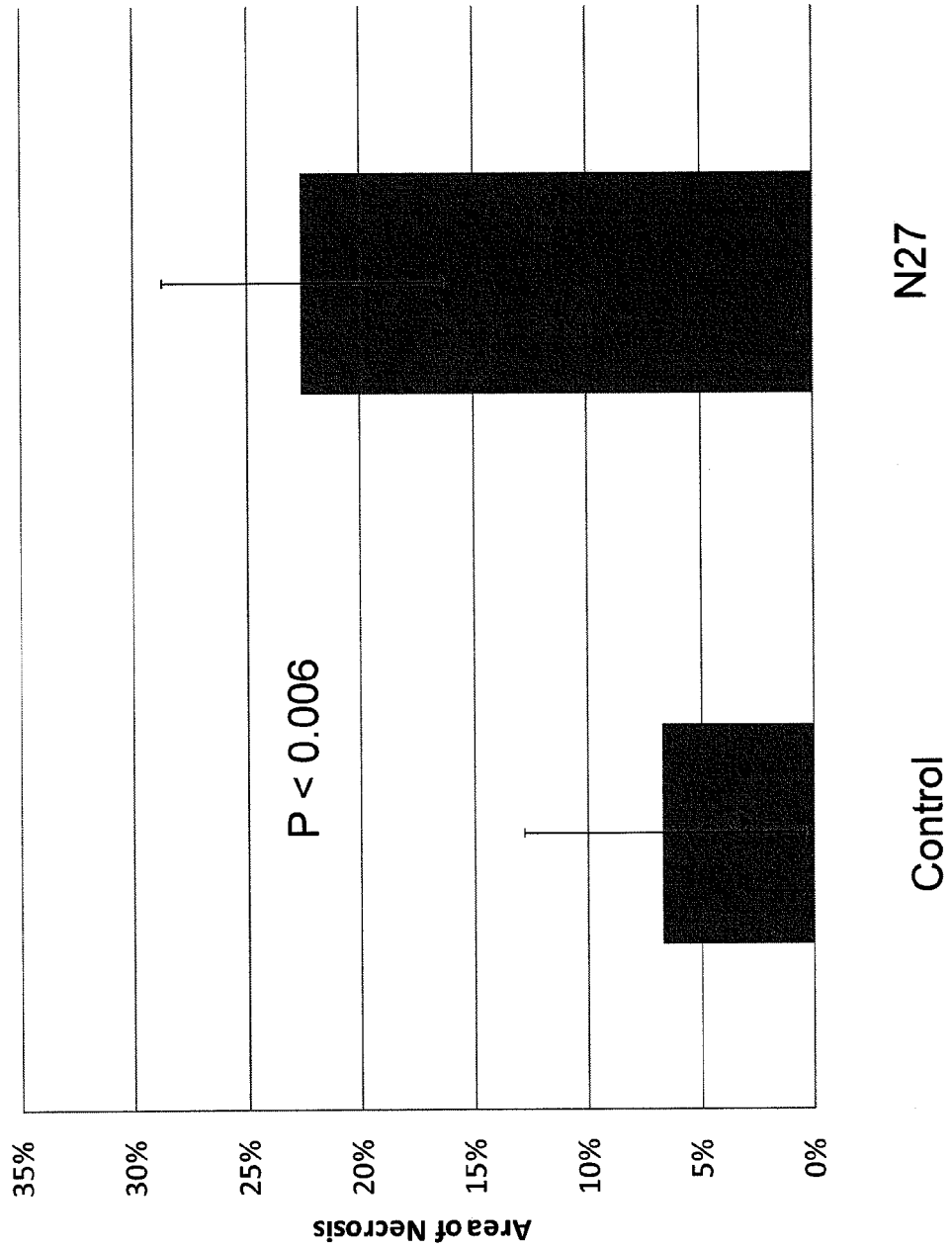
FIG. 8: Comparison of Necrosis in Control and Treated Orthotopic Breast Tumors MDA-MB-231.

To evaluate the effects of agRNA treatment H&E preparations were made. Based on these data, it appeared that there was extensive necrosis in the treatment group in all tumors, whereas there was none in any of the control treated animals. To verify that necrosis was apparent, the inventors performed TUNEL assays on the same series of sections. These data show that all of the treatment group sections exhibited extensive apoptotic cells (fluorescent yellow) whereas none of the control group sections did. To validate these data were repeated the experiment using 10 mice in each group. The results show a statistically significant induction of apoptosis in the treatment group compared to controls (FIG. 8).

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. References

The following references, to the extent that they provide exemplary procedural or other details supplementary to those set forth herein, are specifically incorporated herein by reference.

U.S. Pat. No. 4,415,723
U.S. Pat. No. 4,458,066
U.S. Pat. No. 4,529,561
U.S. Pat. No. 4,737,323
U.S. Pat. No. 5,795,715
U.S. Pat. No. 5,889,136
U.S. Pat. No. 6,747,014
U.S. Pat. No. 6,753,423
Allerson et al., *J. Med. Chem.*, 48:901-904, 2005.
Bakhshi et al., *Cell*, 41(3):899-906, 1985.
Bayne and Allshire, *Trends Genetics*, 21:370-373, 2005.
Bentin and Nielsen, *Biochemistry*, 35:8863-8869, 1996.
Bernstein and Allis, *Genes Dev.*, 19:1635-1655, 2005.
Bloomfield, *Ann. Rev. Biophys. Bioeng.*, 10:421-450, 1981.
Bourdon et al., *Genes Dev.*, 19(18):2122-2137, 2005.
Bumcrot et al., *Nature Chem. Biol.*, 2:711-719, 2006.
Cancer: Principles and Practice of Oncology, Single Volume (Book with CD-ROM), Devita et al., (Eds.), Lippencott, 2001.
Camnan et al., *Science*, 281:1674-1679, 1998.
Caplen et al., *Gene*, 252:95-105, 2000.
Castanotto et al., *Mol. Therapy*, 12:179-183, 2005.
Choung et al., *Biochem. Biophys. Res. Commun.*, 342:919-927, 2006.
Cleary and Sklar, *Proc. Natl. Acad. Sci. USA*, 82(21):7439-7443, 1985.
Cleary et al., *J. Exp. Med.*, 164(1):315-320, 1986.
Crawford and Lamb, *Mol. Biol. Med.*, 2(4):261-72, 1984.
Culver et al., *Science*, 256(5063):1550-1552, 1992.
Dande et al., *J. Med. Chem.*, 49:1624-1634, 2006.
Demidov et al., *ChemBiochem.*, 2:133-139, 2001.
Egholm et al., *Nature*, 365:566-568, 1993.
Elbashir et al., *Nature*, 411(6836):494-498, 2001.
Faruqi et al., *Proc. Natl. Acad. Sci. USA*, 95:398-403, 1998.
Fire et al., *Nature*, 391:806-811, 1998.
Gregoriadis, In: *Liposome Technology*, Vols. 1-3, CRC Press, Boca Raton, Fl, 1993.
Grewal and Moazed, *Science*, 301:798-802, 2003.
Grishok et al., *Science*, 287:2494-2497, 2000.
Haeberli et al., *Nucleic Acids Res.*, 33:3965-3975, 2005.
Hall et al., *Nucleic Acids Res.*, 32:5991-6000, 2004.
Hall et al., *Nucleic Acids Res.*, 34:2773-2781, 2006.
Holstege et al., *EMBO J.*, 16:7468-7480, 1997.
Hope et al., *Biochim. Biophys. Acta*, 812:55-65, 1985.
Hoshika et al., *Nucleic Acids Res.*, 32:3815-3825, 2004.
Janoff, In: *Liposomes: Rational Design*, Marcel Dekker, NY, 1999.
Janowski et al., *Nat. Struct. Mol. Biol.*, 13(9):787-792, 2006.
Janowski et al., *Nature Chem. Biol.*, 1:210-216, 2005b.
Janowski et al., *Nature Chem. Biol.*, 1:216-222, 2005a.
Kahl et al., *J. Mol. Biol.*, 299:75-89, 2000.
Kaihatsu et al., *Chem. Biol.*, 11:749-758, 2004.
Kawasaki and Taira, *Nature*, 431:211-217, 2004.
Kerr et al., *Br. J. Cancer*, 26(4):239-257, 1972.
Ketting et al., *Cell*, 99:133-141, 1999.
Kuwabara et al., *Cell*, 116:779-793, 2004.
Larsen and Nielsen, *Nucl. Acids Res.*, 24:458-463, 1996.
Li et al., *Nat. Med.*, 11:944-951, 2005.
Lin & Avery, *Nature*, 402:128-129, 1999.
Massenegger et al., *Cell*, 76:567-576, 1994.
Mattick and Makunin, *Hum. Mol. Genet.*, 14:R121-132, 2005.
Matzke et al., *Biochim. Biophys. Acta*, 1677:129-141, 2004.
Mollegaard et al., *Proc. Natl. Acad. Sci. USA*, 91:3892-3895, 1994.
Montgomery et al., *Proc. Nat'l Acad. Sci. USA*, 95:155-2-15507, 1998.
Morris et al., *Science*, 305:1289-1292, 2004.
Nielsen et al., *Science*, 254:1497-1500, 1991.
Park et al., *Biochem. Biophys. Res. Comm.*, 323:275-280, 2004.
PCT Appln. WO 00/44914,
PCT Appln. WO 01/36646
PCT Appln. WO 01/68836
PCT Appln. WO 05/115481
PCT Appln. WO 99/32619
Pelissier and Wassenegger, *RNA*, 6:55-65, 2000.
Plasterk and Ketting, *Curr. Opin. Genet. Dev.*, 10:562-567, 2000.
Prakash et al., *Bioorg. Med. Chem. Lett.*, 16:3238-3240, 2006.
Prakash et al., *J. Med. Chem.*, 48:4247-4253, 2005.
Rand et al., *Cell*, 123:621-629, 2005.
Remington's Pharmaceutical Sciences, 15$^{th}$ ed., pages 1035-1038 and 1570-1580, Mack Publishing Company, Easton, Pa., 1980.
Rohaly et al., *Cell*, 122(1): 21-32, 2005.
Schramke et al., *Nature*, 435:1275-1279, 2005.
Shah, In: *Micelles, Microemulsions, and Monolayers: Science and Technology*, Marcel Dekker, NY, 1998.
Sharp and Zamore, *Science*, 287:2431-2433, 2000.
Sharp, *Genes Dev.*, 13:139-141, 1999.
Sigova et al., *Genes Dev.*, 18:2359-2367, 2004.
Smith and Rutledge, *Natl. Cancer Inst. Monogr.*, 42:141-143, 1975.
Somoza et al., *Angew. Chem. Int. Edn. Engl.*, 45:4994-4997, 2006.
Soutschek et al., *Nature*, 432:173-178, 2004.
Sugiyama et al., *Proc. Natl. Acad. Sci. USA*, 102:152-157, 2005.
Svoboda et al., *Nucl. Acids. Res.*, 32:3601-3606, 2004.
Szoka and Papahadjopoulos, *Proc. Natl. Acad. Sci. USA*, 75:4194 4198, 1978.
Tabara et al., *Cell*, 99:123-132, 1999.
Tang, *Trends Biochem. Sci.*, 30:106-114, 2004.
Ting et al., *Nat. Genet.*, 37(8):906-910, 2005.
Toyooka et al., *Hum. Mutat.*, 21(3):229-239, 2003.
Tsujimoto and Croce, *Proc. Natl. Acad. Sci. USA*, 83(14): 5214-5218, 1986.
Tsujimoto et al., *Nature*, 315:340-343, 1985.
Verdel et al., *Science*, 303:672-676, 2003.
Vogelstein et al., *Nature*, 408(6810):307-310, 2000.
Volpe et al., *Science*, 297:1833-1837, 2002.
Wincott et al., *Nucleic Acids Res.*, 23(14):2677-2684, 1995.

Woo et al., *Nature*, 394:700-703, 1998.
Xia et al., *ACS Chem. Biol.*, 1:176-183, 2006.
Young et al., *N Engl J. Med.* 7:299(23):1261-1266, 1978.
Zhang et al., *Cell*, 92:725-734, 1998.
Zhang et al., *Nucl. Acids Res.*, 28:3332-3338, 2000.
Zimmerman et al., *Nature*, 441:111-114, 2006.

What is claimed is:

1. A method of inhibiting a cancer cell expressing a dominant-negative P53 comprising contacting said cancer cell with a duplex RNA of 15-25 bases in length that is homologous to bases −200 to −1 of the p53 promoter located 170 bases 5' relative to DBTSS transcriptional start site, wherein said duplex RNA inhibits expression of a dominant-negative p53 expressed by said cancer cell.

2. The method of claim 1, wherein said cancer cell is a breast cancer cell, a lung cancer cell, a prostate cancer cell, an ovarian cancer cell, a liver cancer cell, a uterine cancer cell, a stomach cancer cell, a colon cancer cell, a cervical cancer cell, a head & neck cancer cell, an esophageal cancer cell, a brain cancer cell, a pancreatic cancer cell, a testicular cancer cell, a skin cancer cell, a lymphoma cell, a leukemia cell, a sarcoma cell or a carcinoma cell.

3. The method of claim 1, wherein said duplex RNA comprises a sequence selected from SEQ ID NOS:1-12.

4. The method of claim 1, wherein said duplex RNA is comprised within a lipid delivery vehicle.

5. The method of claim 1, wherein said duplex RNA has an $IC_{50}$ of $10^{-12}$.

6. The method of claim 1, wherein said duplex RNA further increases the expression of a Δp53 expressed by said cancer cell.

7. The method of claim 1, wherein inhibiting comprises inhibiting cell growth, cell replication, cell survival, metastasis, tissue invasion, or drug resistance.

8. The method of claim 1, wherein inhibiting comprises inducing cell death.

9. A method of increasing the sensitivity of a cancer cell expressing a dominant-negative p53 to an anti-cancer therapy comprising contacting said cancer cell with a duplex RNA of 15-25 bases in length that is homologous to a transcriptional start bases −200 to −1 of the p53 promoter located 5' 170 bases relative to DBTSS transcriptional start site, wherein said duplex RNA inhibits expression of a dominant-negative p53 expressed by said cancer cell.

10. The method of claim 9, wherein said cancer cell is a breast cancer cell, a lung cancer cell, a prostate cancer cell, an ovarian cancer cell, a liver cancer cell, a uterine cancer cell, a colon cancer cell, a stomach cancer cell, a cervical cancer cell, a head & neck cancer cell, an esophageal cancer cell, a brain cancer cell, a pancreatic cancer cell, a testicular cancer cell, a skin cancer cell, a lymphoma cancer cell, a leukemia cell, a sarcoma cell or a carcinoma cell.

11. The method of claim 9, wherein said duplex RNA comprises a sequence selected from SEQ ID NOS:1-12.

12. The method of claim 9, wherein said duplex RNA is comprised within a lipid delivery vehicle.

13. The method of claim 9, wherein said duplex RNA further increases the expression of a Δp53 expressed by said cancer cell.

14. The method of claim 9, wherein said anticancer therapy is a DNA damaging agent therapy.

15. The method of claim 9, wherein said anticancer therapy is chemotherapy or radiotherapy.

16. The method of claim 9, further comprising contacting said cell with said anticancer therapy.

17. A method of altering the expression of p53 isoforms in a cell expressing a dominant-negative p53 comprising contacting said cell with a duplex RNA of 15-25 bases in length that targets bases −200 to −1 of the p53 promoter located 170 bases 5' relative to DBTSS transcriptional start site.

18. The method of claim 17, wherein said duplex RNA comprises a sequence selected from SEQ ID NOS:1-12.

* * * * *

UNITED STATES PATENT AND TRADEMARK OFFICE
CERTIFICATE OF CORRECTION

PATENT NO. : 7,858,592 B2  
APPLICATION NO. : 12/035982  
DATED : December 28, 2010  
INVENTOR(S) : Shames et al.

Page 1 of 1

It is certified that error appears in the above-identified patent and that said Letters Patent is hereby corrected as shown below:

Column 43, line 59 to column 44, line 26, delete "a transcriptional start".

Signed and Sealed this
Twenty-first Day of June, 2011

David J. Kappos
*Director of the United States Patent and Trademark Office*

```
                                SEQUENCE LISTING

<160> NUMBER OF SEQ ID NOS: 21

<210> SEQ ID NO 1
<211> LENGTH: 21
<212> TYPE: DNA
<213> ORGANISM: Artificial
<220> FEATURE:
<223> OTHER INFORMATION: Synthetic primer

<400> SEQUENCE: 1
aatgcaccct cctccccaac t                                             21

<210> SEQ ID NO 2
<211> LENGTH: 21
<212> TYPE: DNA
<213> ORGANISM: Artificial
<220> FEATURE:
<223> OTHER INFORMATION: Synthetic primer

<400> SEQUENCE: 2
aatctgcacc ctcctcccca a                                             21

<210> SEQ ID NO 3
<211> LENGTH: 21
<212> TYPE: DNA
<213> ORGANISM: Artificial
<220> FEATURE:
<223> OTHER INFORMATION: Synthetic primer

<400> SEQUENCE: 3
aaactctgca ccctcctccc c                                             21

<210> SEQ ID NO 4
<211> LENGTH: 21
<212> TYPE: DNA
<213> ORGANISM: Artificial
<220> FEATURE:
<223> OTHER INFORMATION: Synthetic primer

<400> SEQUENCE: 4
aacctgactc tgcaccctcc t                                             21

<210> SEQ ID NO 5
<211> LENGTH: 21
<212> TYPE: DNA
<213> ORGANISM: Artificial
<220> FEATURE:
<223> OTHER INFORMATION: Synthetic primer

<400> SEQUENCE: 5
aaatcctgac tctgcaccct c                                             21

<210> SEQ ID NO 6
<211> LENGTH: 21
<212> TYPE: DNA
<213> ORGANISM: Artificial
<220> FEATURE:
<223> OTHER INFORMATION: Synthetic primer

<400> SEQUENCE: 6
```

| | -continued | |
|---|---|---|
| aagaatcctg actctgcacc c | | 21 |

<210> SEQ ID NO 7
<211> LENGTH: 21
<212> TYPE: DNA
<213> ORGANISM: Artificial
<220> FEATURE:
<223> OTHER INFORMATION: Synthetic primer

<400> SEQUENCE: 7
aagagaatcc tgactctgca c                                          21

<210> SEQ ID NO 8
<211> LENGTH: 21
<212> TYPE: DNA
<213> ORGANISM: Artificial
<220> FEATURE:
<223> OTHER INFORMATION: Synthetic primer

<400> SEQUENCE: 8
aagcgagaat cctgactctg c                                          21

<210> SEQ ID NO 9
<211> LENGTH: 21
<212> TYPE: DNA
<213> ORGANISM: Artificial
<220> FEATURE:
<223> OTHER INFORMATION: Synthetic primer

<400> SEQUENCE: 9
aacggcgaga atcctgactc t                                          21

<210> SEQ ID NO 10
<211> LENGTH: 21
<212> TYPE: DNA
<213> ORGANISM: Artificial
<220> FEATURE:
<223> OTHER INFORMATION: Synthetic primer

<400> SEQUENCE: 10
aagtcggcga gaatcctgac t                                          21

<210> SEQ ID NO 11
<211> LENGTH: 21
<212> TYPE: DNA
<213> ORGANISM: Artificial
<220> FEATURE:
<223> OTHER INFORMATION: Synthetic primer

<400> SEQUENCE: 11
aaaggtcggc gagaatcctg a                                          21

<210> SEQ ID NO 12
<211> LENGTH: 21
<212> TYPE: DNA
<213> ORGANISM: Artificial
<220> FEATURE:
<223> OTHER INFORMATION: Synthetic primer

<400> SEQUENCE: 12
aaccaggtcg gcgagaatcc t                                          21

<210> SEQ ID NO 13
<211> LENGTH: 21
<212> TYPE: DNA
<213> ORGANISM: Artificial

```
<220> FEATURE:
<223> OTHER INFORMATION: Synthetic primer

<400> SEQUENCE: 13
aaagcttctc aaaaagtttt g                                              21

<210> SEQ ID NO 14
<211> LENGTH: 21
<212> TYPE: DNA
<213> ORGANISM: Artificial
<220> FEATURE:
<223> OTHER INFORMATION: Synthetic primer

<400> SEQUENCE: 14
aatgactgtc ggcatccaga a                                              21

<210> SEQ ID NO 15
<211> LENGTH: 21
<212> TYPE: DNA
<213> ORGANISM: Artificial
<220> FEATURE:
<223> OTHER INFORMATION: Synthetic primer

<400> SEQUENCE: 15
aagacggaga gactcgtgac t                                              21

<210> SEQ ID NO 16
<211> LENGTH: 21
<212> TYPE: DNA
<213> ORGANISM: Artificial
<220> FEATURE:
<223> OTHER INFORMATION: Synthetic primer

<400> SEQUENCE: 16
aatggaccca cctgcccatc t                                              21

<210> SEQ ID NO 17
<211> LENGTH: 21
<212> TYPE: DNA
<213> ORGANISM: Artificial
<220> FEATURE:
<223> OTHER INFORMATION: Synthetic primer

<400> SEQUENCE: 17
aacctaccag ggcagctacg g                                              21

<210> SEQ ID NO 18
<211> LENGTH: 21
<212> TYPE: DNA
<213> ORGANISM: Artificial
<220> FEATURE:
<223> OTHER INFORMATION: Artificial primer

<400> SEQUENCE: 18
aaggaaattt gcgtgtggag t                                              21

<210> SEQ ID NO 19
<211> LENGTH: 21
<212> TYPE: DNA
<213> ORGANISM: Artificial
<220> FEATURE:
<223> OTHER INFORMATION: Artificial primer

<400> SEQUENCE: 19
aatctactgg gacggaacag c                                              21
```

```
<210> SEQ ID NO 20
<211> LENGTH: 21
<212> TYPE: DNA
<213> ORGANISM: Artificial
<220> FEATURE:
<223> OTHER INFORMATION: Artificial primer

<400> SEQUENCE: 20
aaaacagctt tgaggtgcgt g                                            21

<210> SEQ ID NO 21
<211> LENGTH: 74
<212> TYPE: DNA
<213> ORGANISM: Artificial
<220> FEATURE:
<223> OTHER INFORMATION: Artificial primer

<400> SEQUENCE: 21
gcacgctccc agcccgaacg caaagtgtcc ccggagccca gcagctacct gctccctgga   60
cggtggctct agac                                                    74
```